ary Examiner—Bernard Dentz
United States Patent
Bosch et al.

(10) Patent No.: US 7,081,533 B2
(45) Date of Patent: Jul. 25, 2006

(54) CYCLOALIPHATIC/AROMATIC DIPHOSPHINES AND USE THEREOF IN CATALYSIS

(75) Inventors: Boris E Bosch, Cologne (DE); Axel Monsees, Frankfurt (DE); Uwe Dingerdissen, Seeheim-Jugenheim (DE); Paul Knochel, Munich (DE); Eike Hupe, Neuried (DE)

(73) Assignee: Degussa AG, Duesseldorf (DE)

( * ) Notice: Subject to any disclaimer, the term of this patent is extended or adjusted under 35 U.S.C. 154(b) by 144 days.

(21) Appl. No.: 10/344,405

(22) PCT Filed: Aug. 17, 2001

(86) PCT No.: PCT/EP01/09481

§ 371 (c)(1),
(2), (4) Date: Jul. 21, 2003

(87) PCT Pub. No.: WO02/14330

PCT Pub. Date: Feb. 21, 2002

(65) Prior Publication Data

US 2004/0019205 A1    Jan. 29, 2004

(30) Foreign Application Priority Data

Aug. 17, 2000   (DE) ................ 100 40 726

(51) Int. Cl.
*C07F 9/46* (2006.01)
*C07F 9/655* (2006.01)
*C07F 15/00* (2006.01)
*C07F 15/04* (2006.01)
*C07F 15/06* (2006.01)

(52) U.S. Cl. .............. 546/21; 548/101; 548/111; 549/6; 549/216; 549/222; 558/85; 558/155; 556/21; 556/23; 568/17

(58) Field of Classification Search .............. 568/17; 558/85, 155; 546/21; 549/6, 216, 222; 548/101, 548/111; 556/21, 23
See application file for complete search history.

(56) References Cited

OTHER PUBLICATIONS

Hupe et al, Organic Letters, 3(1), p. 127-130, Dec. 13, 2000.*
E. Hupe et al.: "Steroselective synthesis of secondary organuzinc reagents and their reaction with heteroaromatic electrophiles" Organic Letters, vol. 3, No. 1, pp. 127-130 2001.
T. Benicori et al.: "2,2', 5,5'-tetramethyl-4,4'-bis(diphenylphosphino)-3,3'-bithiophene: A new, very efficient, easily accessible chiral biheteroaromatic ligand for homohenous stereoselective catalysis" J. Org. Chem., vol. 65, No. 7, pp. 2043-2047 2000.
G. Zhu et al.: "Highley enantioselective rh.-catalyzed hydrogenations with a new chiral 1,4-bisphosphine containing a cyclic backbone" J. Am. Chem. Soc., vol. 119, No. 7, pp. 1799-1800.
M. Cereghetti et al.: "(R)- and (S)-6,6'-dimethyl- and 6,6'-dimethoxy-2,2'-diiodo-1, 1'-biphenyls: versatile intermediates for the synthesis of atropisomeric diphosphine ligands" Tetrahedron Letters, vol. 37, No. 30, pp. 5347-5250 1996.
A. Boudier et al.: "Palladium catalyzed stereoselective cross-couplings and acytations of chiral secondary diorgaozincs" Tetrahedron Letters, vol. 40, pp. 687-690 1999.

* cited by examiner

*Primary Examiner*—Bernard Dentz
(74) *Attorney, Agent, or Firm*—Oblon, Spivak, McClelland, Maier & Neutadts, P.C.

(57) ABSTRACT

The present invention concerns novel unsymmetrical chiral diphosphines of a mixed aliphatic-aromatic type and processes for synthesizing them, complexes of these compounds and their use as catalysts.

Figure 1:
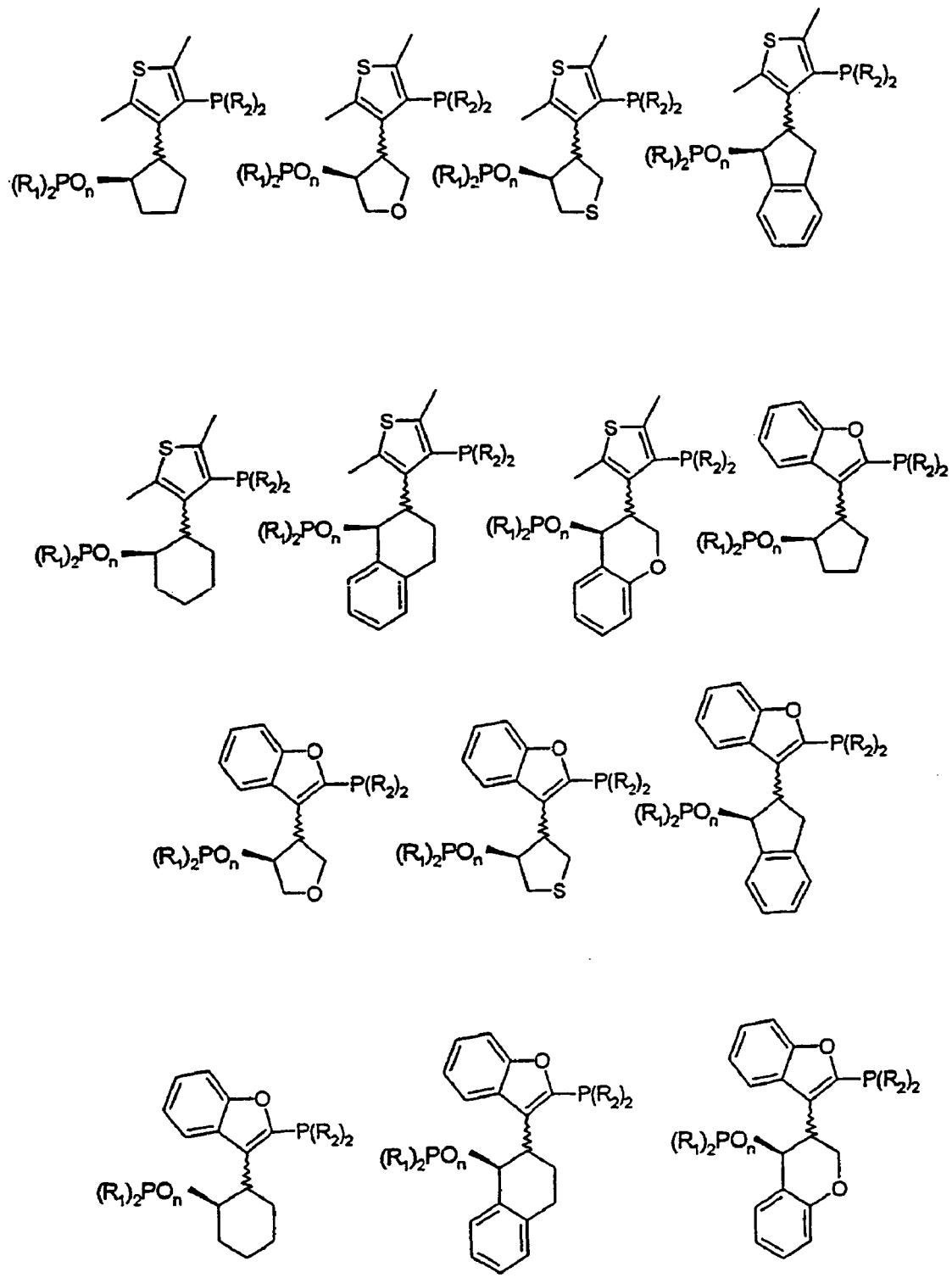

20 Claims, 4 Drawing Sheets where n = 0, 1 where X1, X2, X3 = H, OMe, OEt, F, Me, Et    n = 0, 1 where R = OMe, t-butyl

CYCLOALIPHATIC/AROMATIC DIPHOSPHINES AND USE THEREOF IN CATALYSIS

This application is a national stage entry of PCT/EP01/09481 filed Aug. 17, 2001.

The present invention concerns novel unsymmetrical chiral diphosphines of a mixed aliphatic-aromatic type and processes for synthesizing them, complexes of these compounds and their use as catalysts.

Trisubstituted organophosphorus compounds are of great importance as ligands in homogeneous catalysis. Variation of the substituents on the phosphorus in such compounds enables the electronic and stearic properties of the phosphorus ligand to be influenced in a targeted manner, so that selectivity and activity in homogeneously catalyzed processes can be controlled. Enantiomerically enriched chiral ligands are used in asymmetric synthesis and asymmetric catalysis; their critical factor here is that both the electronic properties and the stereochemical properties of the ligand are optimally matched to the particular catalysis problem. There is a great need for chiral ligands which differ stereochemically or/and electronically so that it is possible to find optimal "tailored" ligands for a particular asymmetric catalysis. The ideal case would therefore be to have a chiral ligand framework which can be modified in a variety of ways and whose stearic and electronic properties can be varied over a wide range.

The structure variety of phosphorus ligands known hitherto is very great. These ligands can be classified, for example, according to class of compound; examples of such classes of compound are trialkylphosphines and triarylphosphines, phosphites, phosphinites, phosphonites, aminophosphines, etc. This classification according to class of compound is particularly useful for describing the electronic properties of the ligands.

Classification of phosphorus ligands according to their symmetry properties or according to the denticity of the ligands is also possible. This structuring takes particular account of the stability, activity and (potential) stereoselectivity of metal complexes bearing phosphorus ligands as catalyst precursors/catalysts. Apart from the widely used $C_2$-symmetric bidentate ligand systems such as DUPHOS, DIPAMP, BINAP or DEGUPHOS, unsymmetrical bidentate organophosphorus ligands are increasingly coming into consideration in asymmetric catalysis. Important examples are the large class of the versatile chiral ferrocenylphosphine ligands such as JOSIPHOS, DPPM, the bisphosphinite ligands such as CARBOPHOS which are, in particular, successfully used in the asymmetric hydrogenation of olefins and imines or the phosphine-phosphite ligands such as BINAPHOS or BIPHEMPHOS, which represent milestones in the asymmetric hydroformylation of olefins. Some structures of phosphorus ligands which have already been used successfully in asymmetric catalysis are shown below.

DIPAMP

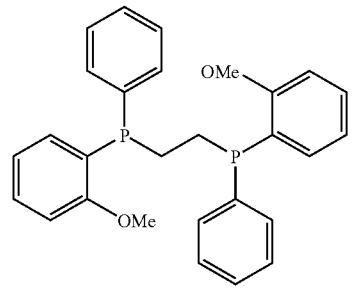

BINAP

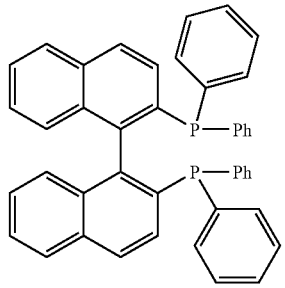

DUPHOS

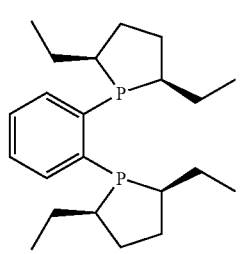

DEGUPHOS

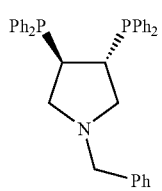

CHIRAPHOS

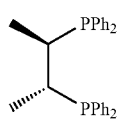

BPPM

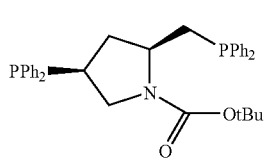

BINAPHOS

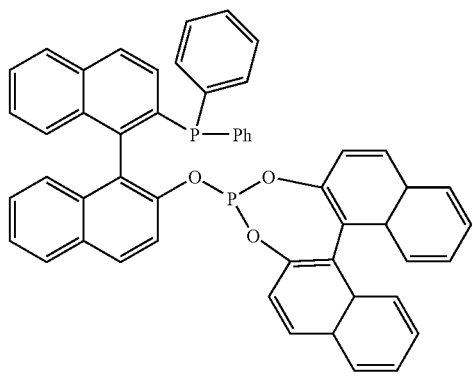

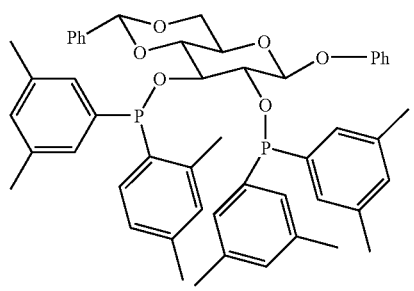

CarboPHOS

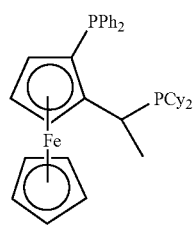

JOSIPHOS

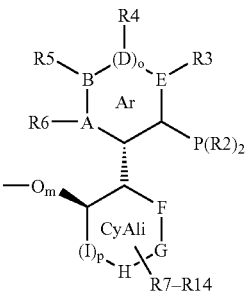

Ia

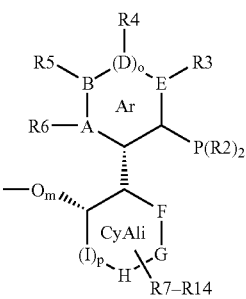

Ib

An important aspect of the success of these classes of compound is believed to be the creation of a particularly asymmetric environment around the metal center by means of these ligand systems. To be able to utilize such an environment for an effective transfer of chirality, it is advantageous to control the flexibility of the ligand system as an inherent limitation of the asymmetric induction.

Disadvantages of the chiral phosphorus ligand systems known hitherto are the relative difficulty of preparing them and the relatively limited opportunities for varying the properties of a given basic ligand framework for a broad range of applications.

It is an object of the present invention to provide novel, unsymmetrical, bidentate and chiral phosphorus ligand systems which combine the abovementioned features for effective asymmetric induction, i.e. a highly asymmetric coordination sphere, with independently modifiable organophosphorus donors, and which can be modified in a simple fashion in terms of their steric and electronic properties over an extraordinarily wide range.

This object is achieved by chiral, unsymmetrical bidentate organophosphorus ligands of the formulae (Ia) and (Ib). The basic framework of the compounds of the invention in each case comprises a chiral cycloaliphatic or heterocycloaliphatic ring system and an aromatic or heteroaromatic ring system which are linked via a direct carbon-carbon single bond. The trivalent phosphorus functions are each bound to this basic framework in the or otho position relative to this bond on the two ring systems.

The present invention accordingly provides compounds of the formulae (Ia) and (Ib), where o and p can each be, independently of one another, 0 or 1, and AR is part of a six-membered aromatic ring system or a 5–6-membered heteroaromatic ring system, where the heteroaromatic ring system can contain 1–3 nitrogen atoms, 1 oxygen atom or 1 sulfur atom in the positions A, B, D and E, and the six-membered heteroaromatic is preferably a pyridyl radical and the five-membered heteroaromatic is preferably a furl, thionyl or payroll group;

Cyan is part of a 5–6-membered cycloaliphatic or heterocycloaliphatic ring system which can contain 1–2 heteroatoms from the group consisting of N, O, S in the positions F, G, H and I, and the cycloaliphatic ring system is preferably a cyclohexyl or cyclopentyl radical or is part of an indenyl or tetrahydronaphthyl radical as fused system and the heteroaliphatic ring system is preferably a tetrahydrofuranyl, tetrahydrothiophenyl, pyrrolidinyl, piperidinyl radical;

$R^1$–$R^2$ are each, independently of one another, $C_1$–$C_{24}$-alkyl, $C_3$–$C_8$-cycloalkyl, where the ring may also contain 1–2 heteroatoms selected from the group consisting of N, O and S; $C_6$–$C_{14}$-aryl, phenyl, naphthyl, fluorenyl, $C_2$–$C_{13}$-heteroaryl in which the number of heteroatoms selected from the group consisting of N, O and S can be 1–4, where the cyclic aliphatic or aromatic radicals are preferably 5- to 6-membered rings; where the abovementioned groups may themselves each be monosubstituted or polysubstituted and these substituents can be, independently of one another, hydrogen, $C_1$–$C_{20}$-alkyl, $C_2$–$C_{20}$-alkenyl, $C_1$–$C_{10}$-haloalkyl, $C_3$–$C_8$-cycloalkyl, $C_2$–$C_9$-heteroalkyl, $C_6$–$C_8$-aryl, phenyl, naphthyl, fluorenyl, $C_2$–$C_6$-heteroaryl, where the number of heteroatoms, in particular from the group consisting of N, O, S, can be 1–4, $C_1$–$C_{10}$-alkoxy, preferably OMe, $C_1$–$C_9$-trihalomethyl-alkyl, preferably trifluoromethyl and trichloromethyl, halo, in particular fluoro and chloro, hydroxyl, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-alkyl$_2$-$C_1$–$C_8$, N-aryl$_2$-$C_5$–$C_6$, N-alkyl$_3$-$C_1$–$C_8^+$, N-aryl$_3$-$C_5$–$C_6^+$, NH—CO-alkyl-$C_1$–$C_8$, NH—CO-aryl-$C_5$–$C_6$, cyano, carboxylato of the formulae COOH and COOQ, where Q is either a monovalent cation or $C_1$–$C_8$-alkyl; $C_1$–$C_6$-acyloxy, sulfinato, sulfonato of the formulae $SO_3H$ and $SO_3Q$, where Q is either a monovalent cation, $C_1$–$C_8$-alkyl or $C_6$-aryl; phosphato of the formulae $PO_3H_2$, $PO_3HQ$ and $PO_3Q_2$, where Q is either a monovalent cation, $C_1$–$C_8$-alkyl or $C_6$-aryl; tri-$C_1$–$C_6$-alkylsilyl, in particular SiMe$_3$, or $R^1$ together with the phosphorus atom or $R^2$ together with the phosphorus atom forms a 4–8-membered aliphatic ring which may be substituted by linear or branched $C_1$–$C_{10}$-alkyl, $C_6$-aryl, benzyl, $C_1$–$C_{10}$-alkoxy, hydroxy or benzyloxy;

$R^3$–$R^{14}$ are each, independently of one another, a hydrogen atom or $C_1$–$C_{24}$-alkyl, $C_1$–$C_{10}$-haloalkyl, $C_3$–$C_8$-cycloalkyl, $C_3$–$C_8$-cycloalkenyl, where the ring may also contain 1–2 heteroatoms selected from the group consisting of N, O and S; $C_6$–$C_{14}$-aryl, phenyl, naphthyl, fluorenyl, $C_2$–$C_{13}$-heteroaryl in which the number of heteroatoms selected from the group consisting of N, O, S can be 1–4, where the cyclic aliphatic or aromatic radicals are preferably 5- to 7-membered rings; where the abovementioned groups may themselves each be monosubstituted or polysubstituted and the substituents can be, independently of one another, hydrogen, $C_1$–$C_{20}$-alkyl, $C_2$–$C_{20}$-alkenyl, $C_1$–$C_{10}$-haloalkyl, $C_3$–$C_8$-cycloalkyl, $C_3$–$C_8$-cycloalkenyl, $C_2$–$C_9$-heteroalkyl, $C_1$–$C_9$-heteroalkenyl, $C_6$–$C_8$-aryl, phenyl, naphthyl, fluorenyl, $C_2$–$C_6$-heteroaryl in which the number of heteroatoms, in particular from the group consisting of N, O, S, can be 1–4, $C_1$–$C_{10}$-alkoxy, $C_1$–$C_9$-trihalomethylalkyl, trifluoromethyl, trichloromethyl, fluoro, chloro, bromo, iodo, hydroxyl, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-alkyl$_2$-$C_1$–$_8$, N-aryl$_2$-$C_5$–$C_6$, N-alkyl$_3$-$C_1$–$C_8^+$, N-aryl$_3$-$C_5$–$C_6^+$, NH—CO-alkyl-$C_1$–$C_8$, NH—CO-aryl-$C_5$–$C_6$, cyano, carboxylato of the formulae COOH and COOQ, where Q is either a monovalent cation or $C_1$–$C_8$-alkyl; $C_1$–$C_6$-acyloxy, sulfinato, sulfonato of the formulae $SO_3H$ and $SO_3Q$, where Q is either a monovalent cation, $C_1$–$C_8$-alkyl or $C_6$-aryl; phosphato of the formulae $PO_3H_2$, $PO_3HQ$ and $PO_3Q_2$, where Q is either a monovalent cation, $C_1$–$C_8$-alkyl or $C_6$-aryl; tri-$C_1$–$C_6$-alkylsilyl; and where two of these substituents can also be bridged, preferably by two adjacent substituents being joined to one another so as to form a 5–7-membered cyclic aromatic or aliphatic compound;

m, n are each, independently of one another, 1 or 0 and P is a trivalent phosphorus atom.

The invention further provides complexes which comprise such a chiral ligand system of the formula (Ia) or (Ib) with at least one metal.

$R^1$–$R^2$ are preferably, independently of one another, $C_1$–$C_6$-alkyl, $C_5$–$C_6$-cycloalkyl, $C_6$-aryl, phenyl, naphthyl, $C_4$–$C_5$-heteroaryl in which the number of heteroatoms selected from the group consisting of N, O, S is 1, where the abovementioned aromatic or heteroaromatic groups may themselves each be monosubstituted to trisubstituted and these substituents can be, independently of one another, hydrogen, $C_1$–$C_6$-alkyl, $C_2$–$C_4$-alkenyl, $C_1$–$C_6$-haloalkyl, $C_2$–$C_6$-heteroalkyl, $C_6$-aryl, phenyl, naphthyl, fluorenyl, $C_3$–$C_5$-heteroaryl in which the number of heteroatoms from the group consisting of N, O, S can be 1–2, $C_1$–$C_6$-alkoxy, preferably OMe, $C_1$–$C_9$-trihalomethylalkyl, preferably trifluoromethyl and trichloromethyl, halo, in particular fluoro and chloro, hydroxyl, trifluoromethyl-sulfonato, oxo, amino, $C_1$–$C_6$-substituted amino of the formulae $NH_2$, NH-alkyl-$C_1$–$C_6$, NH-aryl-$C_6$, N-alkyl$_2$-$C_1$–$C_6$, N-aryl$_2$-$C_6$, N-alkyl$_3$-$C_1$–$C_6^+$, N-aryl$_3$-$C_6^+$, NH—CO-alkyl-$C_1$–$C_6$, NH—CO-aryl-$C_6$, in particular NMe$_2$, NEt$_2$, cyano, carboxylato of the formulae COOH and COOQ, where Q is either a monovalent cation or $C_1$–$C_4$-alkyl; $C_1$–$C_6$-acyloxy, sulfinato, sulfonato of the formulae $SO_3H$ and $SO_3Q$, where Q is either a monovalent cation, $C_1$–$C_4$-alkyl or $C_6$-aryl; phosphato of the formulae $PO_3H_2$, $PO_3HQ$ and $PO_3Q_2$, where Q is either a monovalent cation, $C_1$–$C_4$-alkyl or $C_6$-aryl; tri-$C_1$–$C_6$-alkylsilyl, in particular SiMe$_3$.

Advantages of these ligands is that they can create a highly asymmetric coordination sphere in a metal complex. Due to the ease with which they can be modified, the electronic and steric properties of the ligands can be varied within wide ranges. Thus, for example, the rigidity of the ligand backbone can be altered by introduction of various substituents on the basic structures of the ligands.

The ligand system of the invention preferably has alkyl, alkenyl, cycloalkyl, alkoxy, trialkylsilyl or/and dialkylamino groups in, independently of one another, $R^1$–$R^{14}$; these groups each have from 1 to 20, in particular from 1 to 6, carbon atoms.

Among alkyl and alkoxy substituents, preference is given to methyl, ethyl, n-propyl, 1-methylethyl, n-butyl, 1-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, n-heptyl, n-octyl, n-nonyl, n-decyl, methoxy, ethoxy, 1-propoxy, 2-propoxy, 1-butoxy, 2-butoxy, 1,1-dimethylethoxy.

Among cyclic alkyl substituents, particular preference is given to substituted and unsubstituted cyclopentyl, cyclohexyl and cycloheptyl radicals.

Preferred alkenyl radicals are vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl, 2-heptenyl, 1-octenyl or 2-octenyl. Among cyclic alkenyl substituents, particular preference is given to cyclopentenyl, cyclohexenyl, cycloheptenyl and norbornyl.

Particularly preferred substituents in $R^1$–$R^2$ are 1-methylethyl, cyclohexyl, cyclopentyl, phenyl, 2-methylphenyl, 3,5-dimethylphenyl, 4-methylphenyl, 4-methoxyphenyl, 3,5-bis(trifluoromethyl)phenyl, 4-trifluoromethylphenyl, 3,5-dimethyl-4-methoxyphenyl, 4-phenoxyl, 4-dialkylamino, 2-alkylphenyl, 3-alkylphenyl, 4-alkylphenyl, 2,6-dialkylphenyl, 3,5-dialkylphenyl, 3,4,5-trialkylphenyl, 2-alkoxyphenyl, 3-alkoxyphenyl, 4-alkoxyphenyl, 2,6-dialkoxyphenyl, 3,5-dialkoxyphenyl, 3,4,5-trialkoxyphenyl, 3,5-dialkyl-4-alkoxyphenyl, 3,5-dialkyl-4-dialkylaminophenyl, 4-dialkylamino, where the abovementioned alkyl and alkoxy groups each preferably have from 1 to 6 carbon atoms, 3,5-trifluoromethyl, 4-trifluoromethyl, 2-sulfonyl, 3-sulfonyl, 4-sulfonyl, monohalogenated to tetrahalogenated phenyl and naphthyl. Preferred halogen substituents are F, Cl and Br.

All haloalkyl or/and haloaryl groups preferably have the formulae $CHal_3$, $CH_2CHal_3$, $C_2Hal_5$, where Hal can be, in particular, F, Cl or Br. Particular preference is given to haloalkyl or/and haloaryl groups of the formulae $CF_3$, $CH_2CF_3$, $C_2F_5$.

Figure 2:
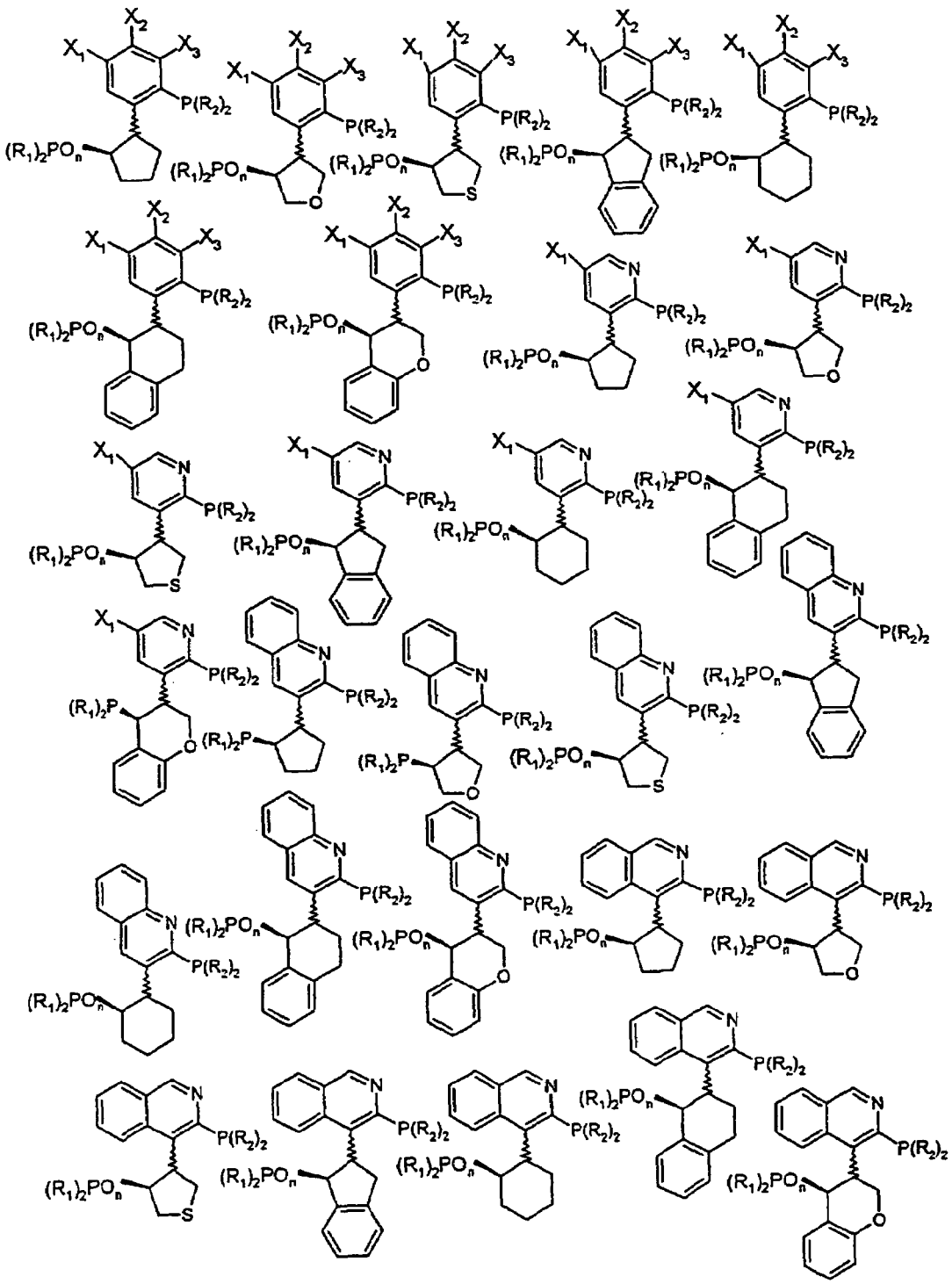
Figure 3:
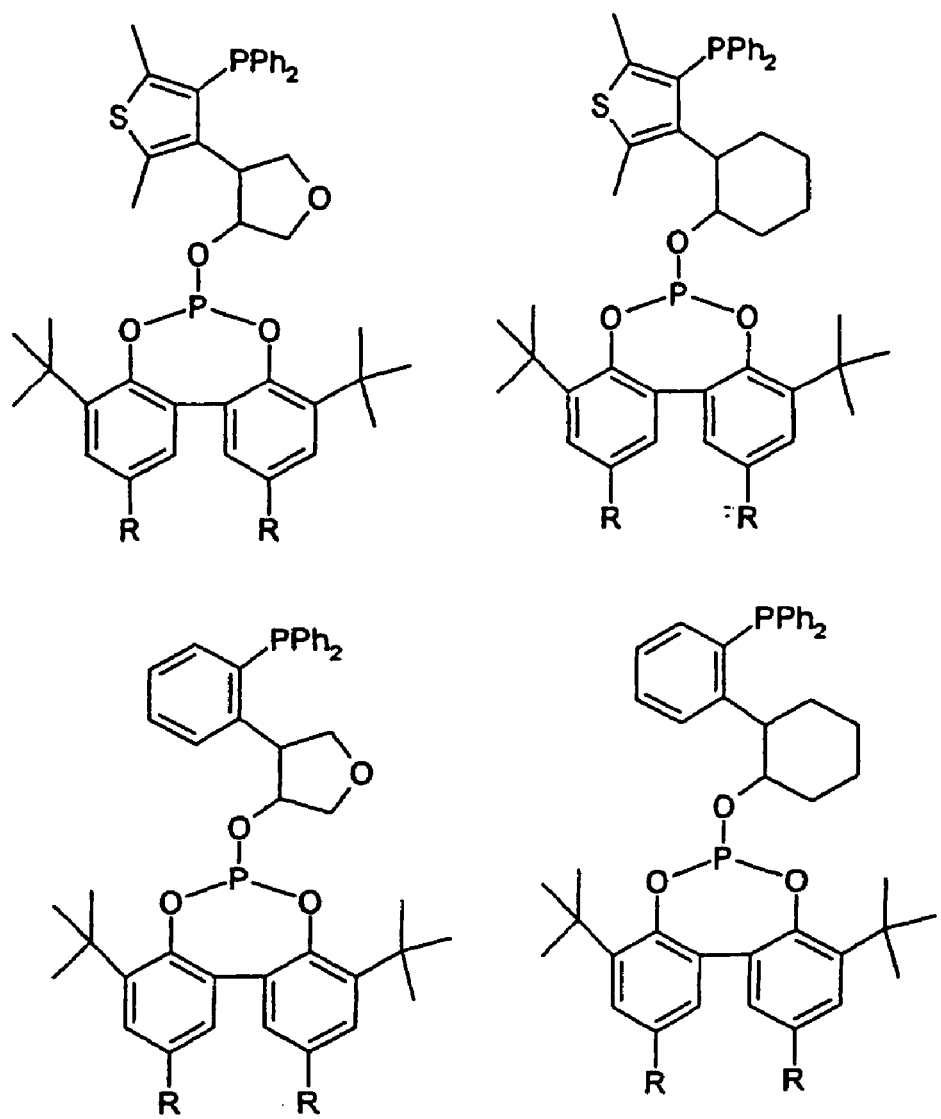

Finally, preference is given to ligand systems of the formulae (Ia) and (Ib) as optically active ligand systems which are enriched in one enantiomer. Particular preference is given to ligand systems in which the enantiomeric enrichment exceeds 90%, in particular 99%. Particularly preferred ligand systems are depicted in FIGS. 1, 2 and 3.

These preferred ligand systems can be prepared by the processes of the invention described below from the following commercially available or readily obtainable basic frameworks:

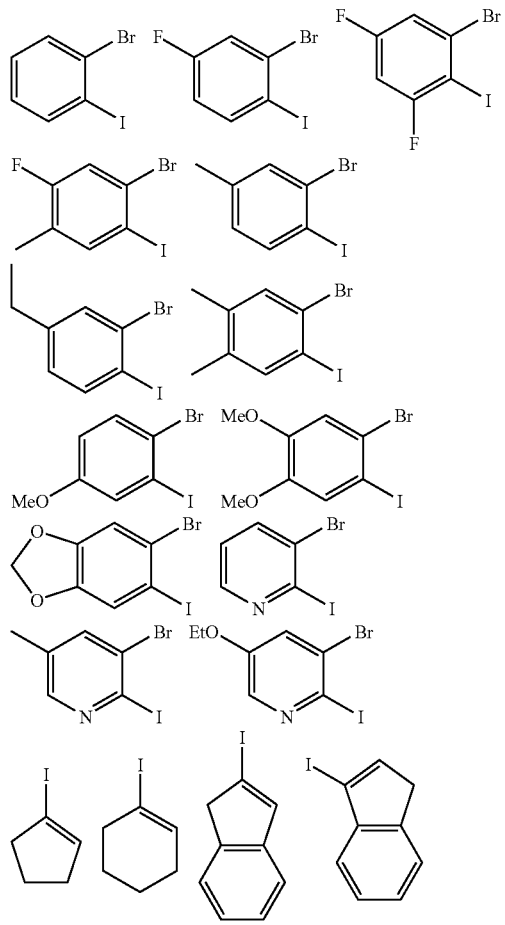

Various methods of synthesizing compounds of the formulae (Ia) and (Ib) are available.

The choice of an appropriate method of preparation is dependent on the availability of the corresponding starting materials and on the desired substitution pattern. Synthetic methods suitable for the purposes of the invention are described below with the aid of simple examples. The processes illustrate the variety of the ligand systems obtainable by these methods. A particularly advantageous aspect of the processes of the invention is that many ligand systems can be obtained in a simple fashion in a few reaction steps.

Preparation of the Bisphosphines

The basic aliphatic-aromatic frameworks are preferably prepared by means of a Negishi cross-coupling of cyclic vinyl iodides and haloaromatics. The introduction of a chiral phosphine unit into the aliphatic system can be achieved in a single-vessel process by asymmetric hydroboration using a chiral borane in a modification of the general literature method (H. C. Brown et al. J. Org. Chem. 1982, 47, 5074). Subsequent transboronation has been found to be advantageous for preparing the compounds of the invention. In one process according to the invention, the chiral borane can be transmetallated by means of diorganozinc compounds without racemization (Micouin, L.; Oestreich, M.; Knochel, P., Angew. Chem., Int. Ed. Engl. 1997, 36, 245–246; A. Boudier, P. Knochel, Tetrahedron Lett. 1999, 40, 687–690) and subsequently be phosphinated with retention of the configuration. The introduction of the second phosphine group can be successfully achieved by bromine/lithium exchange using strong bases (e.g. butyllithium) and subsequent phosphination using a chlorophosphine. Customary methods known from the literature are used for purifying the phosphorus-containing intermediates and the ligands. Inversion at the stereogenic center is achieved by means of a variation of the above-described process. The asymmetric hydroboration is worked up oxidatively and the chiral alcohol is subsequently blocked by means of a base-stable protective group. Bromine/lithium exchange with subsequent phosphination and removal of the protective group gives a chiral phosphino alcohol. Subsequent transformation into an appropriate leaving group and phosphonation under $S_N2$ conditions makes it possible to form the cis-configured bisphosphine with complete stereoinversion.

Preparation of the Phosphine-phosphinites and Phosphine-phosphites

The phosphine-phosphinites and phosphine-phosphites of the invention can be prepared from the chiral alcohols. The chiral alcohols are readily obtainable by means of a Negishi coupling and subsequent asymmetric hydroboration with an oxidative work-up. Nucleophilic ring opening of a meso-epoxide with subsequent resolution of the racemate likewise provides a rapid route to chiral alcohols which serve as basic building blocks for the ligands of the invention. The trans-configured alcohols are reacted in the presence of a nitrogen base and a chlorophosphine to give the phosphinite. These processes can be greatly improved by the use of Grignard compounds as base. This applies particularly to the reaction with aliphatic chlorophosphines. The introduction of the second phosphine group can be achieved by bromine/lithium exchange using strong lithium bases and subsequent phosphination by means of a chlorophosphine. To prepare the cis-configured ligands, an inversion of the stereo center has to be carried out. The inversion can be achieved in one reaction step with the aid of the Mitsunobu reaction or in a two-stage process via oxidation followed by a diastereoselective reduction. After inversion of the stereo center, the phosphinite is formed by the above-described route and the cis-configured phosphine-phosphinite is prepared via bromine/lithium exchange using strong lithium bases and subsequent phosphination by means of a chlorophosphine.

In a preferred process for preparing the phosphine-phosphinites based on 3,5-dimethylthiophene, the chiral alcohol is obtained as described above by epoxide opening and subsequent resolution of the racemate and the hydroxyl function is protected by means of a base-stable protective group. Bromine/lithium exchange, subsequent phosphonation and removal of the protective group gives the chiral phosphino alcohol. In the presence of Grignard reagents, the phosphine-phosphinite is formed in a manner analogous to the process described above.

Figure 4:
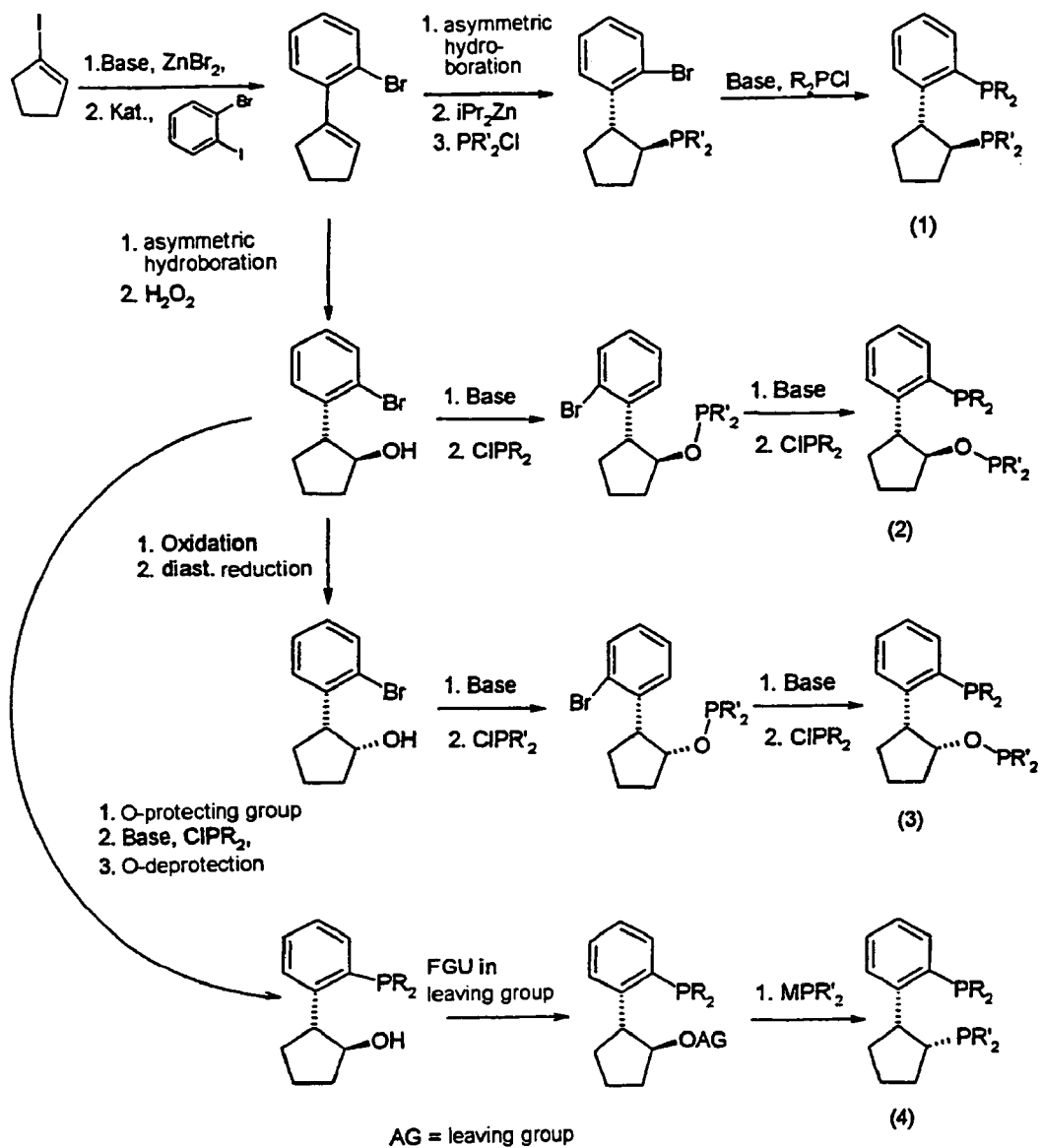

FIG. 4 shows an overview of the individual synthetic routes. In FIG. 4, the substituents denoted as R and R' are generally various substituents described more precisely in the above definition of R1–R2. In the interests of simplicity, simple basic ligand frameworks such as phenylcyclopentyl and thiophenyltetrahydro-furanyl have been chosen in the illustrations, without this implying any restrictions or limitations.

FIG. 4 shows that the ligands of the invention can be synthesized in a simple manner despite the fact that the processes have to tolerate many different substituents. The ligands can be prepared stereoselectively in a three-step process starting from simple starting materials. This makes a synthesis on an industrial scale possible.

In the following, the preparative routes to the ligands of the invention which are outlined in FIG. 4 will be described in more detail for the preferred synthetic processes according to the invention.

Preparation of the Basic Ligand Frameworks:

Synthetic Route A:

The synthesis of the basic aliphatic-aromatic frameworks can be achieved in a single-vessel process by means of Negishi cross-coupling of cyclic vinyl iodides and haloaromatics known from the literature (preparation of the vinyl iodides by known methods, e.g. from ketones using hydrazine/I$_2$/base (Barton, D. K. Tetrahedron 1988, 44, 147–62) or LDA/ClP(O)(OEt)$_2$/ISiMe$_3$ (Lee, K.; Wiemer, D. F. Tetrahedron Lett. 1993, 34, 2433–6).). (Scheme 1).

quent elimination of water. Resolution of the racemic alcohol gives the enantiomerically pure trans-configured alcohol (Scheme 2).

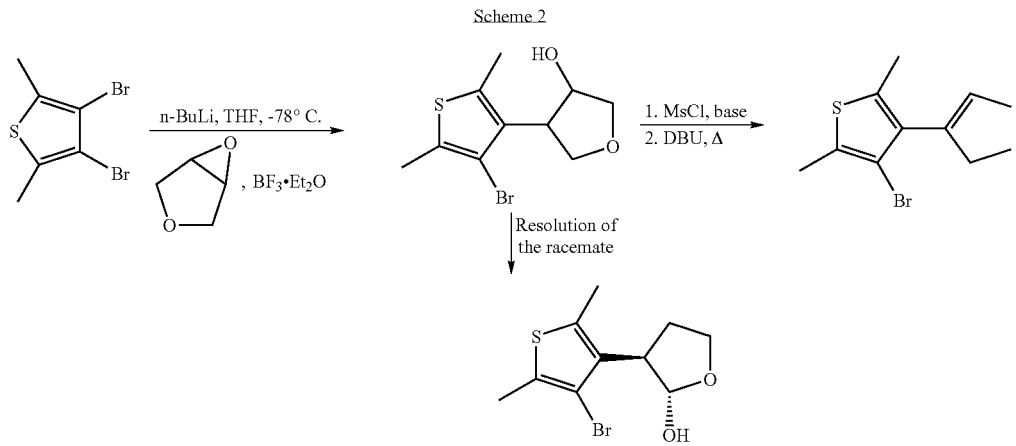

Scheme 2

Synthetic Route B:

As an alternative, the basic frameworks to be used for the purposes of the invention can also be prepared by ring opening of meso-epoxides by means of a base and subse-

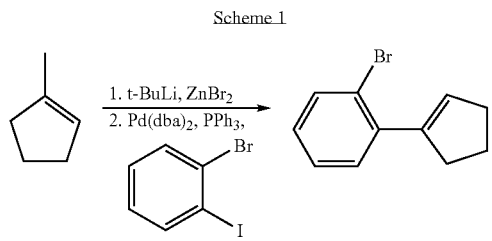

Scheme 1

Phosphinations

Ligands Having a Trans Configuration in the Aliphatic

The introduction of a chiral phosphine unit into the aliphatic system can be achieved in a single-vessel process by asymmetric hydroboration using a chiral borane in a modification of the general literature method (H. C. Brown et al. J. Org. Chem. 1982, 47, 5074). Subsequent transboronation has been found to be advantageous for preparing the compounds of the invention. In one process according to the invention, the chiral borane can be transmetallated by means of diorganozinc compounds without racemization (Micouin, L.; Oestreich, M.; Knochel, P., Angew. Chem., Int. Ed. Engl. 1997, 36, 245–246; A. Boudier, P. Knochel, Tetrahedron Lett. 1999, 40, 687–690) and subsequently be phosphinated with retention of the configuration. Oxidative work-up makes it possible to isolate the desired product (Scheme 3).

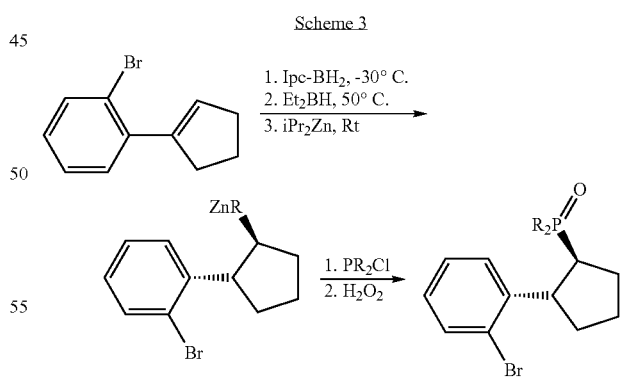

Scheme 3

The introduction of the phosphine unit into the aromatic system can be achieved by variations of methods known from the literature:

The reaction sequence shown below has been found to be a particularly advantageous method of synthesizing the compounds of the invention. It is advantageous to carry out all reaction steps in one vessel without intermediate work-up. (Scheme 4).

Scheme 4

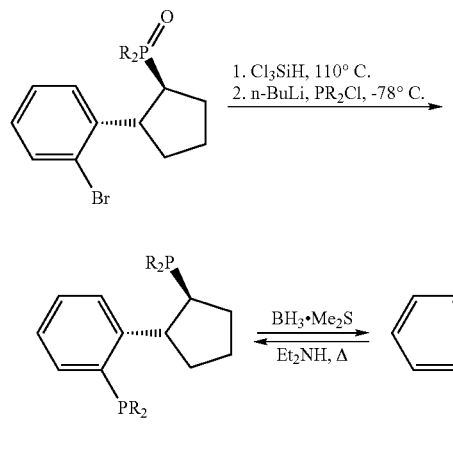

The phosphine oxide is firstly reduced and the aromatic is subsequently subjected to bromine/lithium exchange using n-butyllithium and then phosphinated by means of an appropriate chlorophosphine. The bisphosphine formed can, in the process of the invention, advantageously be isolated as a borane adduct and can subsequently be converted back into the free phosphine in a known manner.

Ligands Having a cis Configuration in the Aliphatic

As an alternative, the chiral borane is converted into the corresponding trans-configured alcohol by means of $H_2O_2$ in a modification of the general literature method (H. C. Brown et al. J. Org. Chem. 1982, 47, 5074), O-protected and phosphinated on the aromatic. The alcohol is set free by means of fluoride. (Scheme 5).

Scheme 5

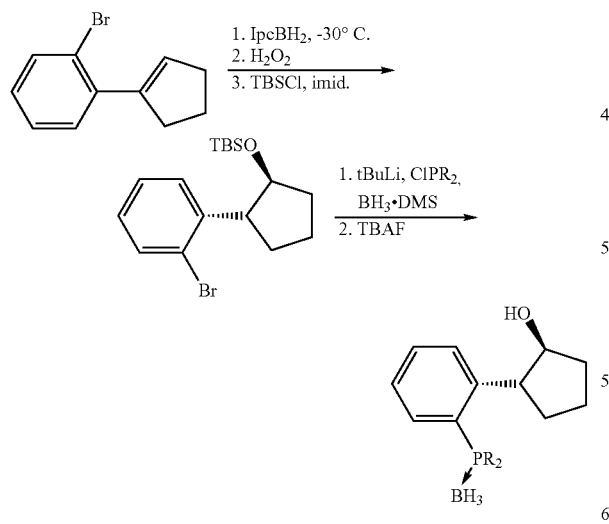

Subsequent transformation into the corresponding mesylate enables the product to be converted into the chiral cis-configured bisphosphine with complete stereoinversion according to the reaction scheme known in principle (e.g. U. Nagel, H. G. Nedden, Chem. Ber./Recueil,. 1997, 130, 385), and this can subsequently be purified by means of an oxidation/reduction sequence or borane protection/removal of the protective group (Scheme 6).

Scheme 6

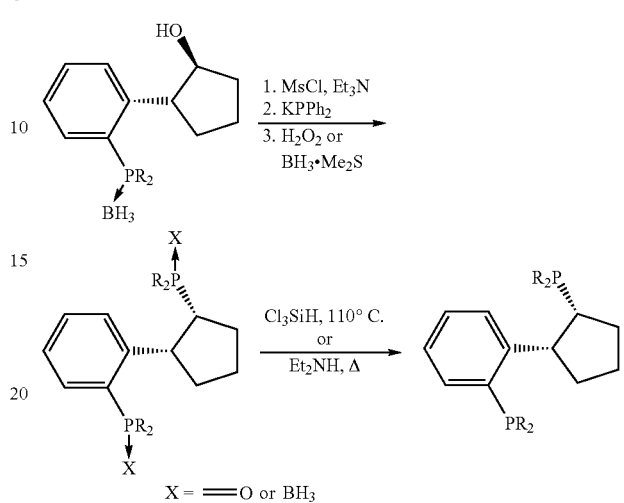

$X = =O$ or $BH_3$

Preparation of Phosphine-phosphinites or Phosphine-phosphites

Corresponding phosphine-phosphinites and phosphine-phosphites according to the invention can be obtained from the chiral phosphino alcohols in a single step by addition of chlorophosphines or chlorophosphites in the presence of stoichiometric amounts of a strong base. It has surprisingly been found that the addition of chlorophosphine by literature methods (procedures for substitution reactions of this type: e.g. Reetz et al. Angew. Chem. 1999, 111, 134; RajanBabu et al., J. Org. Chem. 1997, 62, 6012; Onuma et al. Bull. Chem. Soc. Jpn. 1980, 53, 2012) using triethylamine or pyridine as base precedes to only a very unsatisfactory degree, if at all. Aliphatic chlorophosphines in particular are virtually impossible to prepare in this way. On the other hand, the use of EtMgBr as base makes it possible to prepare and isolate the phosphine-phosphinites of the invention in good to very good yields (Scheme 7).

Scheme 7

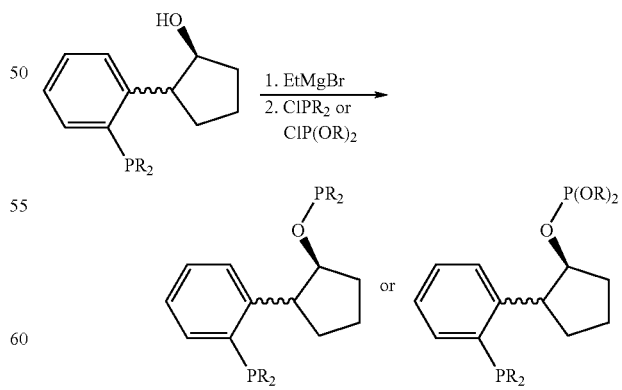

According to the invention, ligands in which the substituents on the two phosphorus units are identical can, as an alternative, be prepared by a more direct route by simultaneous introduction of the radicals in a single-vessel process by means of reaction with 2 equivalents of a strong base (e.g. n-butyllithium or tert-butyllithium) and subsequent reaction with 2 equivalents of the appropriate chlorophosphine (Scheme 8).

Scheme 8

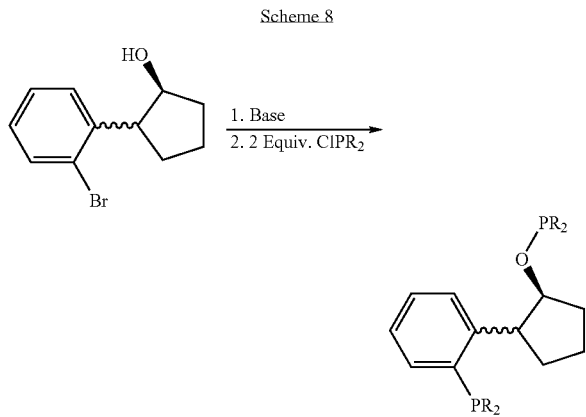

The phosphine-phosphinites of the invention can likewise be obtained by means of a combination of the above-described methods (Scheme 9).

Scheme 9

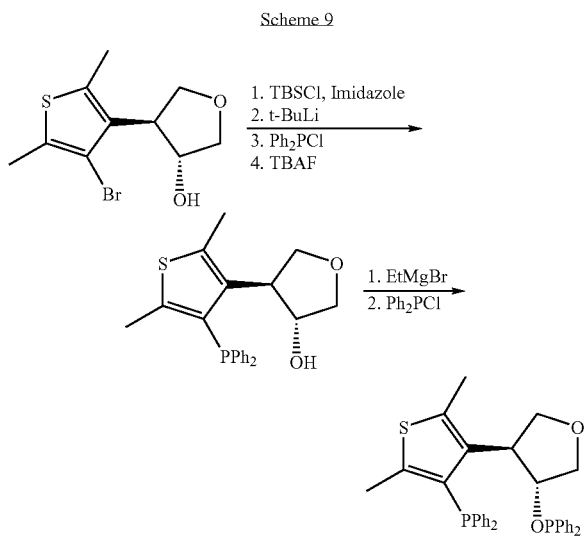

The compounds of the formulae (Ia) and (Ib) can be used as ligands on metals in asymmetric, metal-catalyzed reactions (e.g. hydrogenation, hydroformylation, rearrangement, allylic alkylation, cyclopropanation, hydrosilylation, hydride transfers, hydroborations, hydrocyanations, hydrocarboxylations, aldol reactions or Heck reaction) and in polymerizations. They are particularly useful for asymmetric reactions.

Suitable complexes, in particular complexes of the formula (II), contain novel compounds of the formulae (Ia) and (Ib) as ligands,

   (II)

where, in the formula (II), M is a metal center, preferably a transition metal center, L are identical or different coordinating organic or inorganic ligands and P are novel bidentate organophosphorus ligands of the formulae (Ia) and (Ib), S are coordinating solvent molecules and A are equivalents of noncoordinating anions, where x and y are integers greater than or equal to 1, z, q and r are integers greater than or equal to 0.

The upper limit on the sum y+z+q is imposed by the number of coordination sites available on the metal centers, with not all coordination sites having to be occupied. Preference is given to complexes having an octahedral, pseudooctahedral, tetrahedral, pseudotetrahedral or square planar coordination sphere, which may also be distorted, around the respective transition metal center. The sum y+z+q in such complexes is less than or equal to 6x.

The complexes of the invention contain at least one metal atom or ion, preferably a transition metal atom or ion, in particular an atom or ion of palladium, platinum, rhodium, ruthenium, osmium, iridium, cobalt, nickel or/and copper.

Preference is given to complexes having less than four metal centers, particularly preferably those having one or two metal centers. The metal centers can be occupied by different metal atoms and/or ions.

Preferred ligands L in such complexes are halide, in particular Cl, Br and I, diene, in particular cyclooctadiene, norbornadiene, olefin, in particular ethylene and cyclooctene, acetato, trifluoroacetato, acetylacetonato, allyl, methallyl, alkyl, in particular methyl and ethyl, nitrile, in particular acetonitrile and benzonitrile, and also carbonyl and hydrido ligands.

Preferred coordinating solvents S are amines, in particular triethylamine, alcohols, in particular methanol, and aromatics, in particular benzene and cumene.

Preferred noncoordinating anions A are trifluoroacetate, trifluoromethanesulfonate, $BF_4$, $ClO_4$, $PF_6$, $SbF_6$ and $BAr_4$.

In the individual complexes, different molecules, atoms or ions of the individual constituents M, P, L, S and A may be present.

Among ionic complexes, preference is given to compounds of the type [RhP(diene)]$^+$A$^-$, where P is a novel ligand of the formula (Ia) or (Ib).

The preparation of these metal-ligand complexes can be carried out in situ by reaction of a metal salt or an appropriate precursor complex with the ligands of the formulae (Ia) and (Ib). A metal-ligand complex can also be obtained by reaction of a metal salt or an appropriate precursor complex with the ligands of the formulae (Ia) and (Ib) and subsequent isolation.

Examples of metal salts are metal chlorides, bromides, iodides, cyanides, nitrates, acetates, acetylacetonates, hexafluoroacetylacetonates, tetrafluoroborates, perfluoroacetates or triflates, in particular of palladium, platinum, rhodium, ruthenium, osmium, iridium, cobalt, nickel or/and copper.

Examples of precursor complexes are:
cyclooctadienepalladium chloride, cyclooctadienepalladium iodide, 1,5-hexadienepalladium chloride, 1,5-hexadienepalladium iodide, bis(dibenzylideneacetone)palladium, bis(acetonitrile)palladium(II) chloride, bis(acetonitrile)palladium(II) bromide, bis(benzonitrile)palladium(II) chloride, bis(benzonitrile)palladium(II) bromide, bis(benzonitrile)palladium(II) iodide, bis(allyl)palladium, bis(methallyl)palladium, allylpalladium chloride dimer, methallylpalladium chloride dimer, tetramethylethylenediaminepalladium dichloride, tetramethylethylenediaminepalladium dibromide, tetramethylethylenediaminepalladium diiodide, tetramethylethylenediaminedimethylpalladium, cyclooctadieneplatinum chloride, cyclooctadieneplatinum iodide, 1,5-hexadieneplatinum chloride, 1,5-hexadieneplatinum iodide, bis(cyclooctadiene)platinum, potassium ethylenetrichloroplatinate, cyclooctadienerhodium(I) chloride dimer, norbornadienerhodium(I) chloride dimer, 1,5-hexadienerhodium(I) chloride dimer, tris(triphenylphosphine)rhodium(I) chloride, hydridocarbonyltris(triphenylphosphine)rhodium(I) chloride, bis(cyclooctadiene) rhodium(I) perchlorate, bis(cyclooctadiene)rhodium(I) tetrafluoroborate, bis(cyclooctadiene)rhodium(I) triflate, bis(acetonitrile) (cyclooctadiene)rhodium(I) perchlorate, bis(acetonitrile) (cyclooctadiene)rhodium(I) tetrafluoroborate, bis(acetonitrile)(cyclooctadiene)rhodium(I) triflate, cyclopentadienerhodium(III) chloride dimer, pentamethylcyclopentadienerhodium(III) chloride dimer, (cyclooctadiene)Ru($\eta^3$-allyl)$_2$, ((cyclooctadiene)Ru)$_2$tetraacetate, ((cyclooctadiene)Ru)$_2$tetra(trifluoroacetate), (arene)RuCl$_2$dimer, tris(triphenylphosphine)ruthenium (II) chloride, cyclooctadieneruthenium(II) chloride, (arene)OsCl$_2$dimer, cyclooctadieneiridium(I) chloride dimer, bis(cyclooctene)iridium(I) chloride dimer, bis(cyclooctadiene)nickel, (cyclododecatriene)nickel, tris(norbornene)nickel, nickel tetracarbonyl, nickel(II) acetylacetonate, (arene)copper triflate, (arene)copper perchlorate, (arene)copper trifluoroacetate, cobalt octacarbonyl.

The complexes based on one or more metallic elements, in particular metals of the group consisting of Ru, Co, Rh, Ir, Ni, Pd, Pt, Cu, may themselves be catalysts or can be used for preparing catalysts based on one or more metallic elements, in particular metals of the group consisting of Ru, Co, Rh, Ir, Ni, Pd, Pt, Cu. All these complexes are particularly useful in the asymmetric hydrogenation of C=C, C=O or C=N bonds, in which they display high activities and selectivities, and in asymmetric hydroformylation. Here, it is found to be particularly advantageous that the ligands of the formulae (Ia) and (Ib) can be modified by simple means in a wide variety of ways so as to match them sterically and electronically to the respective substrate and the catalytic reaction.

Appropriate catalysts comprise at least one of the complexes of the invention.

Some nonrestrictive examples are given below to illustrate the invention.

EXAMPLES

General

Reactions of air-sensitive compounds were carried out in an argon-filled glove box or in standard Schlenk tubes. Tetrahydrofuran (THF), diethyl ether and dichloromethane solvents were degassed and dried by means of a solvent drying unit (Innovative Technologies) by filtration through a column filled with activated aluminum oxide; toluene and pentane were additionally freed of oxygen by means of a column filled with a copper catalyst.

The following examples serve to illustrate the invention. They do not imply any restriction.

Example 1

1-(Cyclopenten-1-yl)-2-bromobenzene t-BuLi (32 mmol, 2 equivalents) is slowly added at −78° C. to cyclopentenyl iodide (16 mmol) in THF (16 ml). After 1 hour at this temperature, a 1 M solution of ZnBr$_2$ in THF (16 ml) is added thereto. The mixture is stirred for 30 minutes at −40° C. and for a further 30 minutes at RT.

In parallel, Pd(dba)$_2$ (6 mol %) and PPh$_3$ (12 mol %) are stirred in THF (16 ml) for 10 minutes at RT. The 2-bromo-1-iodobenzene (16 mmol, 1 equivalent) is added to this solution. The mixture is stirred for another 10 minutes at RT. The solution obtained in this way is transferred by means of a syringe to the other solution. The mixture is stirred at 50° C. for 12 hours. After work-up by extraction (Et$_2$O/NaCl), the desired product 1-(cyclopenten-1-yl)-2-bromobenzene is obtained from the ether phase, purified by column chromatography (pentane) and isolated in a yield of 61%.

$^1$H NMR (CDCl$_3$): δ=7.43 (d, 1H), 7.20–7.10 (m, 2H), 6.87 (m, 1H), 5.88 (d, 1H), 2.65 (m, 2H), 2.43 (m, 2H), 1.95 (m, 2H) ppm.

Example 2

1-(Cyclopentyl-2-diphenylphosphinoxy)-2-bromobenzene 1-(Cyclopenten-1-yl)-2-bromobenzene (1 mmol) in THF (0.5 ml) is added at −30° C. to a solution of freshly prepared IpcBH$_2$ (1M in THF, 1 ml) over a period of 30 minutes. The mixture is stirred at this temperature for 2 days. The solvent is then removed in a high vacuum and the borane obtained is reacted with Et$_2$BH solution (1 m, 7.3 M in DMS) at 50° C. for 12 hours. After removal of the solvent in a high vacuum, Zn(iPr)$_2$ (2.25 ml, 4 M in Et$_2$O) is added thereto. The resulting solution is stirred at RT for 5 hours. After 3 hours in a high vacuum, the grayish black residue in the flask is taken up in THF (2 ml) and centrifuged under argon. The clear supernatant solution is transferred by means of a syringe, cooled to 0° C. and Ph$_2$PCl (4 mmol) is slowly added. The mixture is stirred at RT for 4 days. After careful addition of H$_2$O$_2$ (1 ml, 30% strength), the mixture is stirred at RT for 30 minutes. Work-up by extraction (CH$_2$Cl$_2$/NaCl) and purification by column chromatography (CH$_2$Cl$_2$/MeOH 49:1) gave the desired diastereomerically pure product in a total yield of 45%.

$^1$H NMR (CD$_3$OD): δ=7.92–7.30 (m, 14H), 4.05 (m, 1H), 3.41 (m, 1H), 2.33–1.51 (m, 6H) ppm.

$^{31}$P NMR (CD$_3$OD): δ=38.7 (s, 1P) ppm.

Example 3

1-(Cyclopentyl-[2-diphenylphosphinoxy])-2-diphenylphosphinobenzene 1-(Cyclopentyl-2-diphenylphosphinoxy)-2-bromobenzene (0.4 mmol) is dissolved in 9 ml of toluene and refluxed with Cl$_3$SiH (10 equivalents) for 12 hours. After this time, a high vacuum is applied for 2 hours. Further toluene (10 ml) and degassed KOH solution (2 M, 10 ml) are added thereto. After removal of the aqueous phase, the organic phase is dried over MgSO$_4$. The suspension is filtered under argon, the solvent is removed in a high vacuum and the colorless residue is taken up in THF (6 ml). The solution is cooled to −78° C. and admixed with n-BuLi (1.2 equivalents). After 2 hours at this temperature, Ph$_2$PCl (1.2 equivalents) is added. Slow thawing to RT (7 hours) is followed by addition of BH$_3$DMS (10 equivalents). The solution is stirred at RT for 12 hours. After work-up in CH$_2$Cl$_2$/NaCl solution, the crude product is purified by column chromatography (CH$_2$Cl$_2$/pentane, then CH$_2$Cl$_2$) and the purified product is obtained in a total yield of 76%.

$^1$H NMR (CDCl$_3$) of borane adduct: δ=7.62–6.90 (m, 24H), 4.25 (m, 1H), 3.31 (m, 1H), 2.18–1.01 (m, 6H) ppm.

$^{31}$P NMR (CDCl$_3$) of borane adduct: δ=25.0 (s, 1P), 20.5 (s, 1P) ppm.

$^{31}$P NMR (CDCl$_3$): δ=−4.2 (d, J=5.7 Hz, 1P), −17.4 (d, J=5.7 Hz, 1P) ppm.

Example 4 trans-4-(4-Bromo-2,5-dimethyl-3-thienyl)tetrahydro-3-furanol

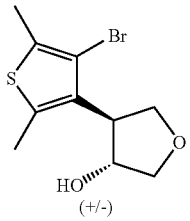

(+/−)

n-Butyllithium (1.6 M in hexane; 0.239 mol) is added dropwise to a solution of 3,4-dibromo-2,5-dimethylthiophene (0.239 mol) in 325 ml of THF which has been cooled to −78° C. and the mixture is stirred for 30 minutes. 3,4-Epoxytetrahydrofuran (0.217 mol) and boron trifluoride etherate (0.217 mol) are added dropwise to this solution. The reaction solution is warmed to 0° C. and stirred for a further 3 hours. It is subsequently hydrolyzed with saturated ammonium chloride solution and the aqueous phase is extracted twice with tert-butyl methyl ether. After drying, the solvent is removed under reduced pressure and the crude product is purified by chromatography. The product is obtained as an oil in a yield of 64%.

$^1$H NMR (CDCl$_3$): δ=4.82 (q, 1H), 4.29–4.21 (m, 2H), 4.11 (t, 1H), 3.99 (dd, 1H), 3.67–3.60 (m, 1H), 2.50 (s, 3H), 2.41 (s, 3H) ppm.

Example 5

(3R,4S)-4-(Bromo-2,5-dimethyl-3-thienyl)-tetrahydro-3-furanol and (3S,4R)-4-(bromo-2,5-dimethyl-3-thienyl)tetrahydro-3-furanol acetate

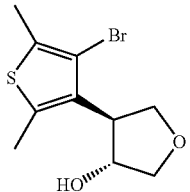

Solid Novozym 435 is added to a solution of trans-4-(4-bromo-2,5-dimethyl-3-thienyl)tetrahydro-3-furanol (0.153 mol) in 425 ml of vinyl acetate and the mixture is subsequently stirred for 24 hours. The enzyme is removed by filtration and the residue is washed with tert-butyl methyl ether. After removal of the solvent, the two products are separated by means of chromatography. (3R,4S)-4-(Bromo-2,5-dimethyl-3-thienyl)tetrahydro-3-furanol is obtained in a yield of 49% (>99% ee) and (3S,4R)-4-(bromo-2,5-dimethyl-3-thienyl)tetrahydro-3-furanol acetate is obtained in a yield of 50% (>97% ee).

$^1$H NMR (CDCl$_3$): δ=5.65–5.60 (m, 1H), 4.44 (dd, 1H), 4.26 (t, 1H), 4.07 (d, 1H), 4.03 (d, 1H), 3.82 (ddd, 1H), 2.51 (s, 3H), 2.46 (s, 3H), 2.17 (s, 3H) ppm.

Example 6

(3R,4S)-4-(Bromo-2,5-dimethyl-3-thienyl)-tetrahydro-3-furanyl tert-butyldimethylsilyl ether

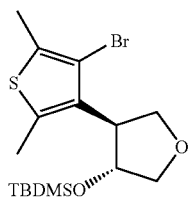

tert-Butyldimethylsilyl chloride (82 mmol) and imidazole (97 mmol) are added to a solution of [lacuna] (75 mmol) in 200 ml of dichloromethane which has been cooled to 0° C. and the reaction solution is warmed to room temperature overnight. The reaction solution is hydrolyzed by means of 150 ml of 1 M hydrochloric acid and the aqueous phase is extracted three times with dichloromethane. The combined organic phases are washed with saturated sodium hydrogen carbonate solution. After drying, the solvent is removed under reduced pressure and the product is obtained as an orange oil in quantitative yield.

$^1$H NMR (CDCl$_3$): δ=4.9 (q, 1H), 4.28–4.18 (m, 3H), 3.82 (dd, 1H), 3.68 (ddd, 1H), 2.54 (s, 3H), 2.47 (s, 3H), 0.96 (s, 9H), 0.04 (s, 3H), 0.00 (s, 3H) ppm.

Example 7

1-(t-Butyl-1,1-dimethylsilyl) (3R,4S)-4-(4-(1,1-di(3,5-di(trifluoromethyl)phenyl)phosphino)-2,5-dimethyl-3-thienyl)tetrahydro-3-furanyl ether

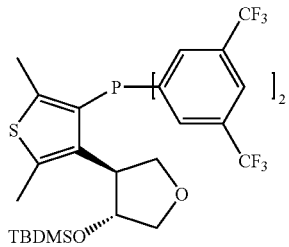

tert-Butyllithium (25.5 mmol) are added at −78° C. to a solution of (3R,4S)-4-(bromo-2,5-dimethyl-3-thienyl)-tetrahydro-3-furanyl tert-butyldimethylsilyl ether (12.8 mmol) in 50 ml of THF over a period of 10 minutes and the mixture is subsequently stirred for 1 hour. 15.3 mmol of bis(3,5-di(trifluoromethyl)phenyl)chlorophosphine are added dropwise to this solution and the reaction solution is warmed to RT overnight. It is subsequently hydrolyzed with degassed water, the solution is diluted with dichloromethane and the aqueous phase is extracted twice with dichloromethane. After drying and removal of the solvent, the crude product is purified by chromatography and crystallized from cold pentane. The product is obtained in a yield of 22%.

$^1$H NMR (C$_6$H$_6$): δ=7.86 (t, 4H), 7.79 (s, 2H), 4.92–4.99 (m, 1H), 4.41 (dd, 1H), 4.30–4.23 (m, 1H), 4.11–4.01 (m, 2H), 3.97 (dd, 1H), 2.22 (s, 3H), 1.60 (s, 3H), 0.99 (s, 9H), 0.00 (s, 3H), −0.04 (s, 3H) ppm.

Example 8

1-(t-Butyl-1,1-dimethylsilyl) (3R,4S)-4-(4-(1,1-di(o-tolyl)phosphino)-2,5-dimethyl-3-thienyl)tetrahydro-3-furanyl ether

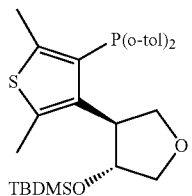

The synthesis is carried out by a method analogous to Example 7.

Yield: 59%

$^1$H NMR (C$_6$H$_6$): δ=7.00–7.30 (m, 8H), 4.90–5.11 (m, 1H), 4.52 (dd, J=10, 8 Hz, 1H), 4.15–4.40 (m, 3H), 4.07 (dd, J=10, 3 Hz, 1H), 2.51 (s, 3H), 2.47 (s, 3H), 2.40 (s, 3H), 1.88 (s, 3H), 1.06 (s, 9H), 0.00 (s, 6H) ppm.

$^{31}$P NMR (C$_6$H$_6$): δ=−22.0 ppm.

Example 9

1-(t-Butyl-1,1-dimethylsilyl) (3R,4S)-4-(4-(1,1-di(p-(fluoro)phenyl)phosphino)-2,5-dimethyl-3-thienyl)tetrahydro-3-furanyl ether

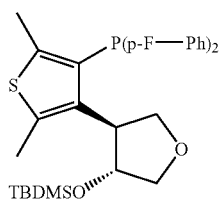

The synthesis is carried out by a method analogous to Example 7.

Yield: 37%

$^1$H NMR (C$_6$H$_6$): δ=7.43–7.52 (m, 4H), 7.27 (q, J=8 Hz, 4H), 4.98–5.03 (m, 1H), 4.48 (dd, J=10, 8 Hz, 1H), 4.32 (dt, J=9, 2 Hz, 1H), 4.17 (t, J=9 Hz, 1H), 4.00–4.08 (m, 1H), 3.93 (dd, J=8, 3 Hz, 1H), 2.69 (s, 3H), 2.01 (s, 3H), 1.01 (s, 9H), 0.03 (s, 3H), 0.00 (s, 3H) ppm.

$^{31}$P NMR (C$_6$H$_6$): δ=−25.3 ppm.

Example 10

1-(t-Butyl-1,1-dimethylsilyl) (3R,4S)-4-(4-(1,1-di(3,5-di(methyl)phenyl)phosphino)-2,5-dimethyl-3-thienyl)tetrahydro-3-furanyl ether

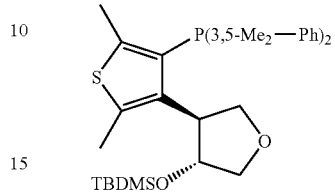

The synthesis is carried out by a method analogous to Example 7.

Yield: 6%

$^1$H NMR (C$_6$H$_6$): δ=7.34 (t, J=8 Hz, 4H), 6.88 (s, 1H), 6.84 (s, 1H), 5.23–5.28 (m, 1H), 4.64 (dd, J=10, 8 Hz, 1H), 4.57 (t, J=9 Hz, 1H), 4.40 (dt, J=8, 2 Hz, 1H), 4.07–4.19 (m, 2H), 2.34 (s, 3H), 2.20 (s, 6H), 2.14 (s, 6H), 2.12 (s, 3H), 1.02 (s, 9H), 0.03 (s, 3H), 0.00 (s, 3H) ppm.

$^{31}$P NMR (C$_6$H$_6$): δ=−10.9 ppm.

Example 11

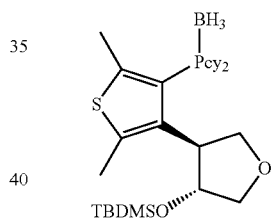

tert-Butyllithium (25.5 mmol) is added at −78° C. to a solution of (3R,4S)-4-(bromo-2,5-dimethyl-3-thienyl)tetrahydro-3-furanyl tert-butyldimethylsilyl ether (12.8 mmol) in 50 ml of THF over a period of 10 minutes and the mixture is subsequently stirred for 1 hour. 15.3 mmol of dicyclohexylchlorophosphine are added dropwise to this solution and the reaction solution is warmed to RT over a period of 2 hours. The solution is subsequently cooled back down to −78° C. and 5 equivalents of borane (1 M in THF) are added. The solution is subsequently warmed to RT and hydrolyzed with degassed water, the solution is diluted with dichloromethane and the aqueous phase is extracted twice with dichloromethane. After drying and removal of the solvent, the crude product is purified by chromatography and crystallized from cold pentane. The product is obtained in a yield of 58%.

$^1$H NMR (C$_6$H$_6$): δ=4.89 (q, J=7 Hz, 1H), 4.17–4.28 (m, 1H), 4.63 (t, J=8 Hz, 1H), 4.20–4.26 (m, 1H), 3.93 (t, J=8 Hz, 1H), 3.76 (dd, J=9, 8 Hz, 1H), 2.44 (s, 3H), 2.29 (s, 3H), 2.13–2.39 (m, 2H), 1.09–2.00 (m, 20H), 0.97 (s, 9H), 0.00 (s, 6H) ppm.

$^{31}$P NMR (C$_6$H$_6$): δ=39.1 ppm.

Example 12

(3R,4S)-4-(4-{1,1-Di[3,5-di(trifluoromethyl)phenyl]phosphino}-2,5-dimethyl-3-thienyl)tetrahydro-3-furanol

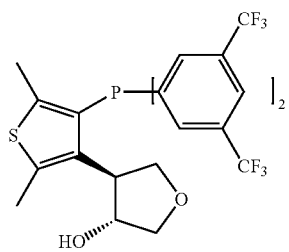

Tetrabutylammonium fluoride solution (5.7 mmol) is added dropwise at 0° C. to a solution of 1-(t-butyl-1,1-dimethylsilyl) (3R,4S)-4-(4-(1,1-di(3,5-di(trifluoromethyl)phenyl)phosphino)-2,5-dimethyl-3-thienyl)tetrahydro-3-furanyl ether (2.86 mmol) in 22 ml of tetrahydrofuran and the mixture is warmed to RT overnight. The solvent is removed under reduced pressure and the crude product is purified by chromatography and isolated in a yield of 87%.

$^1$H NMR (C$_6$H$_6$): δ=8.08 (t, 6H), 7.97 (s, 1H), 7.92 (s, 1H), 4.45–4.38 (m, 1H), 4.10 (dd, 1H), 4.01–3.92 (m, 1H), 3.89–3.82 (m, 1H), 3.58 (dd, 1H), 2.29 (s, 3H), 2.15 (s, 3H) ppm.

$^{31}$P NMR (C$_6$H$_6$) δ=−9.93 (s, 1P) ppm.

Example 13

(3R,4S)-4-(4-{1,1-Di[o-tolyl]phosphino}-2,5-dimethyl-3-thienyl)tetrahydro-3-furanol

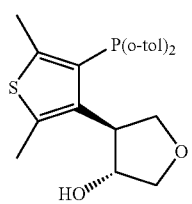

The synthesis is carried out by a method analogous to Example 12.

Yield: 93%

$^1$H NMR (CDCl$_3$): δ=7.46–7.54 (m, 4H), 7.38 (t, J=7 Hz, 2H), 7.29 (dd, J=8, 6 Hz, 1H), 7.20 (dd, J=8, 6 Hz, 1H), 4.68–4.84 (m, 1H), 4.34–4.41 (m, 1H), 4.03–4.12 (m, 2H), 3.83–3.93 (m, 2H), 2.69 (s, 3H), 2.57 (s, 3H), 2.56 (s, 3H), 2.26 (s, 3H), 1.60 (br s, 1H) ppm.

Example 14

(3R,4S)-4-(4-{1,1-Di[3,5-di(methyl)phenyl]-phosphino}-2,5-dimethyl-3-thienyl)tetrahydro-3-furanol

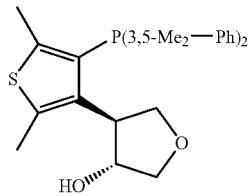

The synthesis is carried out by a method analogous to Example 12.

Yield: 99%

$^1$H NMR (CDCl$_3$): δ=7.32 (d, J=7 Hz, 2H), 7.30 (d, J=7 Hz, 2H), 6.78 (s, 2H), 4.64 (q, J=7 Hz, 1H), 4.22 (dd, J=11, 9 Hz, 1H), 4.00–4.09 (m, 2H), 3.88–3.96 (m, 1H), 3.76 (dd, J=11, 4 Hz, 1H), 2.40 (s, 3H), 2.27 (s, 3H), 2.10 (s, 6H), 2.08 (s, 6H) ppm.

Example 15

(3R,4S)-4-(4-{1,1-di[3,5-di(p-(fluoro)phenyl)]phosphino}-2,5-dimethyl-3-thienyl)tetrahydro-3-furanol

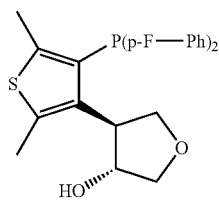

The synthesis is carried out by a method analogous to Example 12.

Yield: 99%

$^1$H NMR (C$_6$H$_6$): δ=7.30–7.40 (m, 4H), 6.93–7.02 (m, 4H), 4.72–4.77 (m, 1H), 4.33 (dd, J=11, 9 Hz, 1H), 4.09–4.20 (m, 2H), 3.98–4.06 (m, 1H), 3.89 (dd, J=10, 4 Hz, 1H), 2.43 (s, 3H), 2.10 (s, 3H), 1.32 (br s, 1H) ppm.

Example 16

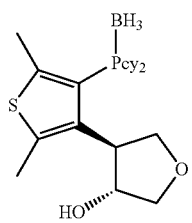

The synthesis is carried out by a method analogous to Example 12.

Yield: 76%

$^1$H NMR (C$_6$H$_6$): δ=4.28 (t, J=9 Hz, 1H), 4.18–4.24 (m, 1H), 3.90–4.03 (m, 1H), 3.87 (dd, J=11, 8 Hz, 1H), 3.70 (t,

J=7 Hz, 1H), 3.56 (dd, J=10, 5 Hz, 1H), 2.70 (s, 3H), 2.50–2.64 (m, 1H), 2.12–2.23 (m, 1H), 2.03 (s, 3H), 0.88–1.98 (m, 20H) ppm.

Example 17 trans-4-(4-Bromo-2,5-dimethyl-3-thienyl)tetrahydro-3-pyranol

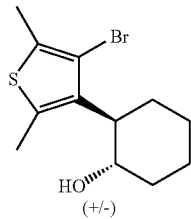

The synthesis is carried out by a method analogous to Example 4.

Yield: 64%

$^1$H NMR (CDCl$_3$): δ=4.25–4.62 (br m, 1H), 2.92–3.11 (br m, 1H), 2.64 (br s, 3H), 2.55 (s, 3H), 2.30–2.40 (m, 1H), 1.48–2.11 (m, 7H) ppm.

Example 18

(3R,4S)- and (3S,4R)-4-(Bromo-2,5-dimethyl-3-thienyl)tetrahydro-3-pyranol acetate

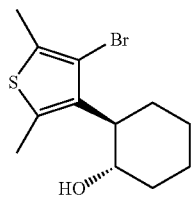

The synthesis is carried out by a method analogous to Example 5 using ChiroCLEC PC $^1$H NMR (CDCl$_3$): δ=5.40–5.54 (br m, 1H), 3.03–3.15 (br m, 1H), 2.50 (s, 3H), 2.42 (s, 3H), 2.20–2.28 (m, 1H), 1.91 (s, 3H), 1.81–2.00 (m, 3H), 1.38–1.66 (m, 4H) ppm.

Example 19

(3R,4S)-4-(Bromo-2,5-dimethyl-3-thienyl)tetrahydro-3-pyranyl tert-butyldimethylsilyl ether

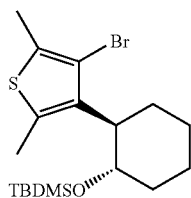

The synthesis is carried out by a method analogous to Example 6.

Yield: 78%

$^1$H NMR (CDCl$_3$): δ=4.13–4.28 (m, 1H), 2.73–2.90 (m, 1H), 2.43 (s, 3H), 2.38 (s, 3H), 2.03–2.10 (m, 1H), 1.66–1.88 (m, 3H), 1.27–1.48 (m, 4H), 0.78 (s, 9H), 0.00 (s, 3H), −0.28 (s, 3H) ppm.

Example 20

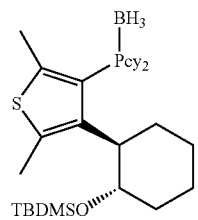

The synthesis is carried out by a method analogous to Example 11.

Yield: 78%

$^1$H NMR (CDCl$_3$): δ=3.93 (dt, J=10, 4 Hz, 1H), 2.40 (s, 3H), 2.37–2.41 (m, 1H), 2.16 (s, 3H), 2.01–2.12 (m, 1H), 0.90–1.96 (m, 29H), 0.80 (s, 9H), 0.00 (s, 3H), −0.18 (s, 3H) ppm.

Example 21

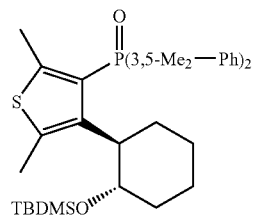

tert-Butyllithium (10.0 mmol) is added at −78° C. to a solution of (3R,4S)-4-(bromo-2,5-dimethyl-3-thienyl)-2-cyclohexyl tert-butyldimethylsilyl ether (5.0 mmol) in 20 ml of THF over a period of 10 minutes and the mixture is subsequently stirred for 1 hour. 6 mmol of bis(3,5-dimethylphenyl)chlorophosphine are added dropwise to this solution and the reaction solution is warmed to RT overnight. The solution is subsequently hydrolyzed by means of hydrogen peroxide solution, stirred for another 2 hours, the solution is diluted with dichloromethane and the aqueous phase is extracted twice with dichloromethane. After drying and removal of the solvent, the crude product is purified by chromatography and recrystallized from cold pentane. The product is obtained in a yield of 59%.

$^1$H NMR (CDCl$_3$): δ=7.30–7.38 (m, 3H), 7.10–7.22 (m, 3H), 3.93 (dt, J=11, 5 Hz, 1H), 2.50–2.60 (m, 1H), 2.48 (s, 3H), 2.37 (s, 12H), 2.22 (s, 3H), 1.07–1.80 (m, 5H), 0.83–0.96 (m, 1H), 0.80 (s, 9H), 0.65–0.77 (m, 1H), 0.50–0.60 (m, 1H), 0.00 (s, 3H), −0.13 (s, 3H) ppm.

Example 22

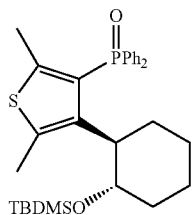

The synthesis is carried out by a method analogous to Example 21.
Yield: 55%
$^1$H NMR (d$^6$-DMSO): δ=7.77–7.88 (m, 10H), 4.10 (dt, J=10, 4 Hz, 1H), 2.84–2.93 (m, 1H), 2.60 (s, 3H), 2.25 (s, 3H), 1.90–1.99 (m, 1H), 1.28–1.70 (m, 6H), 0.91 (s, 9H), 0.54–0.69 (m, 1H), 0.16 (s, 3H), 0.00 (s, 3H) ppm.

Example 23

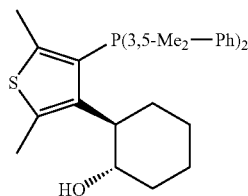

A solution of 2.89 mmol of the phosphine oxide (Example 22) and 28.9 mmol of trichlorosilane in 10 ml of toluene are refluxed for 3 hours and subsequently cooled to RT. The reaction mixture is hydrolyzed by means of 30% strength sodium hydroxide solution, stirred at RT for 30 minutes and diluted with 30 ml of water. The aqueous phase is extracted twice with TBME. After drying and removal of the solvent, the crude product is purified by chromatography. The product is obtained in a yield of 77%.
$^1$H NMR (d$^6$-DMSO): δ=6.90–7.00 (m, 6H), 4.09–4.23 (m, 1H), 3.76 (br s, 1H), 2.95–3.08 (m, 1H), 2.43 (s, 3H), 2.30 (s, 6H), 2.28 (s, 6H), 1.92–2.00 (m, 1H), 1.90 (s, 3H), 0.96–1.70 (m, 7H) ppm.
$^{31}$P NMR (d$^6$-DMSO): δ=−24.8, −26.1 ppm.

Example 24

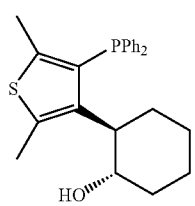

The synthesis is carried out by a method analogous to Example 23.
Yield: 69%
$^1$H NMR (d$^6$-DMSO): δ=7.27–7.40 (m, 10H), 4.10–4.27 (m, 1H), 3.80 (br s, 1H), 3.00–3.10 (m, 1H), 2.42 (s, 3H), 1.90–2.00 (m, 1H), 1.78 (s, 3H), 1.00–1.70 (m, 7H) ppm.
$^{31}$P NMR (d$^6$-DMSO): δ=−24.4, −26.0 ppm.

Example 25

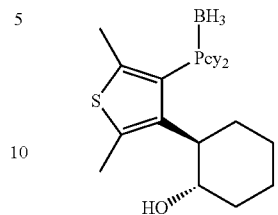

The synthesis is carried out by a method analogous to Example 12.
Yield: 27%
$^1$H NMR (C$_6$H$_6$): δ=3.73–3.83 (m, 1H), 3.28 (br s, 1H), 2.70 (br s, 3H), 2.13–2.27 (m, 1H), 2.10 (s, 3H), 2.00–2.06 (m, 1H), 1.93 (s, 3H), 1.80–1.87 (m, 1H), 0.95–1.73 (m, 27H) ppm.
$^{31}$P NMR (C$_6$H$_6$): δ=36.7 ppm.

Example 26

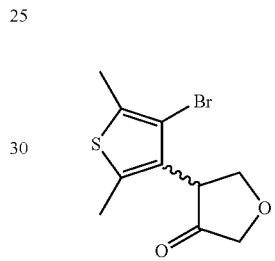

A solution of 92.4 mmol of oxalyl chloride in 400 ml of dichloromethane is cooled to −50° C. and 185 mmol of DMSO are added over a period of 5 minutes. After 5 minutes, 77 mmol of the alcohol (Example 5) dissolved in 100 ml of dichloromethane are added. The solution is stirred for a further 30 minutes and 385 mmol of triethylamine are subsequently added and the reaction solution is warmed to RT. The organic phase is washed with 200 ml of water, 200 ml of 3 M hydrochloric acid and 200 ml of sodium hydrogen carbonate solution. The organic phase is dried, the solvent is removed under reduced pressure and the crude product is used in the next stage.
$^1$H NMR (CDCl$_3$): δ=4.44 (t, J=12 Hz, 1H), 4.20 (t, J=11 Hz, 1H), 4.13 (d, J=12 Hz, 2H), 3.86 (t, J=11 Hz, 1H), 2.27 (s, 3H), 2.26 (s, 3H) ppm.

Example 27

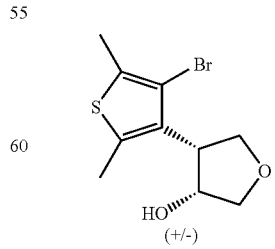

77 mmol of the ketone (Example 26) are dissolved in 200 ml of THF. 100 mmol of K-Selectrid are added at −78° C.

and the solution is warmed to RT overnight. 150 ml of ethanol are added to this solution, and 150 ml of 4N sodium hydroxide solution and 30% strength hydrogen peroxide are added in succession. The solution is stirred for a further 2 hours, diluted with 250 ml of TBME and the phases are separated. The aqueous phase is extracted twice with 100 ml of TBME, the organic phase is subsequently dried and the solvent is removed under reduced pressure. The crude product is recrystallized from heptane.

Yield: 69%

$^1$H NMR (CDCl$_3$): δ=4.65–4.70 (m, 1H), 4.56 (t, J=11 Hz, 1H), 4.23 (dd, J=12, 5 Hz, 1H), 4.18 (t, J=10 Hz, 1H), 4.11 (d, J=12 Hz, 1H), 3.82–3.90 (m, 1H), 2.68 (s, 3H), 2.52 (s, 3H), 1.78 (br s, 1H) ppm.

Example 28

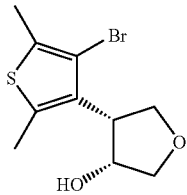

The synthesis is carried out by a method analogous to Example 5 using ChiroCLEC PC.

$^1$H NMR (CDCl$_3$): δ=5.60–5.64 (m, 1H), 4.54 (t, J=10 Hz, 1H), 4.26 (dd, J=12, 5 Hz, 1H), 4.10–4.21 (m, 2H), 3.98–4.06 (m, 1H), 2.63 (m, 3H), 2.50 (m, 3H), 2.03 (m, 3H) ppm.

Example 29

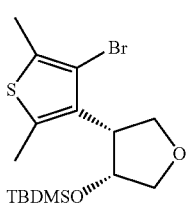

The synthesis is carried out by a method analogous to Example 6.

Yield: 95%

$^1$H NMR (CDCl$_3$): δ=4.85 (dt, J=6, 2 Hz, 1H), 4.67 (dd, J=13, 11 Hz, 1H), 4.36 (dd, J=13, 6 Hz, 1H), 4.26 (t, J=11 Hz, 1H), 4.08 (dd, J=10, 2 Hz, 1H), 3.78–3.96 (m, 1H), 2.70 (s, 3H), 2.60 (s, 3H), 1.00 (s, 9H), 0.11 (s, 3H), 0.00 (s, 3H) ppm.

Example 30

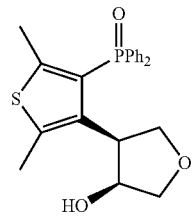

The synthesis is carried out by a method analogous to Example 21 and Example 12.

Yield: 37%

$^1$H NMR (C$_6$H$_6$): δ=7.80–7.94 (m, 4H), 7.18–7.31 (m, 6H), 4.93 (q, J=8 Hz, 1H), 4.62 (dd, J=11, 8 Hz, 1H), 4.40–4.45 (m, 1H), 4.31 (dd, J=11, 8 Hz, 1H), 4.25 (q, J=8 Hz, 1H), 3.97 (t, J=11 Hz, 1H), 2.62 (s, 3H), 1.79 (s, 3H) ppm.

$^{31}$P NMR (C$_6$H$_6$): δ=40.4 ppm.

Example 31

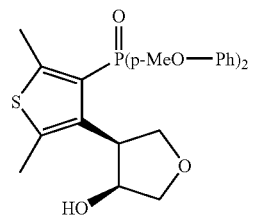

The synthesis is carried out by a method analogous to Example 21 and Example 12.

Yield: 35%

$^1$H NMR (C$_6$H$_6$): δ=7.60–7.73 (m, 4H), 6.68–6.73 (m, 4H), 6.14 (br s, 1H), 4.85 (q, J=7 Hz, 1H), 4.58 (dd, J=9, 7 Hz, 1H), 4.30 (dd, J=10, 8 Hz, 1H), 4.14–4.23 (m, 2H), 3.89 (t, J=9 Hz, 1H), 3.23 (s, 3H), 3.22 (s, 3H), 2.47 (s, 3H), 1.82 (s, 3H) ppm.

$^{31}$P NMR (C$_6$H$_6$): δ=40.3 ppm.

Example 32

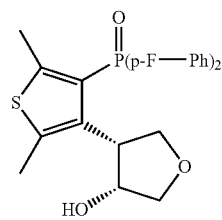

The synthesis is carried out by a method analogous to Example 21 and Example 12.

Yield: 40%

$^1$H NMR (CDCl$_3$): δ=7.42–7.52 (m, 4H), 7.04–7.12 (m, 4H), 4.23 (q, J=7 Hz, 1H), 4.10 (dd, J=9, 8 Hz, 1H), 3.96 (dd,

J=10, 7 Hz, 1H), 3.63–3.70 (m, 2H), 3.58 (t, J=9 Hz, 1H), 2.40 (s, 3H), 2.23 (br s, 1H), 1.59 (s, 3H) ppm.
$^{31}$P NMR (CDCl$_3$): δ=27.3 ppm.

Example 33

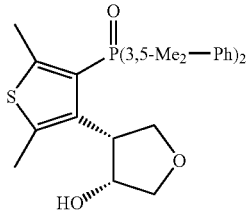

The synthesis is carried out by a method analogous to Example 21 and Example 12.
Yield: 45%
$^1$H NMR (CDCl$_3$): δ=7.06–7.14 (m, 6H), 4.20 (q, J=8 Hz, 1H), 4.12 (dd, J=10, 11 Hz, 1H), 3.96 (dd, J=11, 9 Hz, 1H), 3.65–3.76 (m, 2H), 3.60 (t, J=10 Hz, 1H), 2.45 (s, 3H), 2.28 (s, 6H), 2.27 (s, 6H), 1.61 (s, 3H) ppm.
$^{31}$P NMR (CDCl$_3$): δ=30.0 ppm.

Example 34

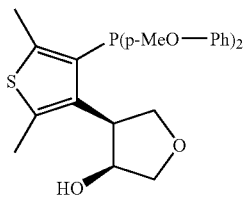

The synthesis is carried out by a method analogous to Example 23.
Yield: 43%
$^1$H NMR (C$_6$H$_6$): δ=7.48–7.55 (m, 4H), 6.94 (d, J=9 Hz, 2H), 6.88 (d, J=9 Hz, 2H), 4.52 (t, J=9 Hz, 1H), 4.21–4.30 (m, 1H), 4.05–4.10 (m, 1H), 4.00 (t, J=9 Hz, 1H), 3.77–3.80 (m, 2H), 3.45 (s, 3H), 3.43 (s, 3H), 2.62 (s, 3H), 2.40 (s, 3H), 1.66 (br s, 1H) ppm.
$^{31}$P NMR (C$_6$H$_6$): δ=−11.5 ppm.

Example 35

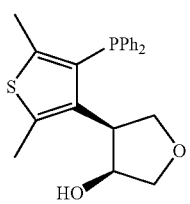

The synthesis is carried out by a method analogous to Example 23.
Yield: 51%
$^1$H NMR (C$_6$H$_6$): δ=7.43–7.50 (m, 4H), 7.03–7.20 (m, 6H), 4.35 (t, J=8 Hz, 1H), 3.90–3.98 (m, 2H), 3.82 (t, J=9 Hz, 1H), 3.60 (dd, J=11, 5 Hz, 1H), 3.32–3.37 (m, 1H), 2.52 (s, 3H), 2.35 (s, 3H), 1.33 (br s, 1H) ppm.
$^{31}$P NMR (C$_6$H$_6$): δ=−11.6 ppm.

Example 36

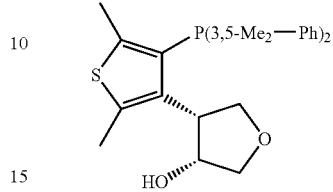

The synthesis is carried out by a method analogous to Example 23.
Yield: 56%
$^1$H NMR (C$_6$H$_6$): δ=7.33 (d, J=9 Hz, 4H), 6.86 (s, 1H), 6.80 (s, 1H), 4.49 (t, J=8 Hz, 1H), 4.12–4.21 (m, 1H), 3.98–4.03 (m, 2H), 3.68 (dd, J=11, 5 Hz, 1H), 3.49–3.54 (m, 1H), 2.58 (s, 6H), 2.19 (s, 6H), 2.12 (s, 6H), 1.56 (br s, 1H) ppm.
$^{31}$P NMR (C$_6$H$_6$): δ=−12.1 ppm.

Example 37

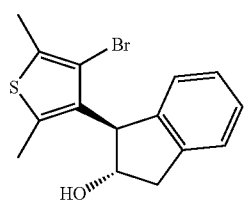

The synthesis is carried out by a method analogous to Example 4 and Example 5 using ChiroCLEC PC.
$^1$H NMR (d$^6$-DMSO): δ=7.05–7.23 (m, 3H), 6.76 (d, J=9 Hz, 1H), 4.68–4.76 (m, 1H), 4.47 (d, J=7 Hz, 1H), 3.28 (dd, J=18, 9 Hz, 1H), 3.18 (br s 1H), 2.90 (dd, J=8, 18 Hz, 1H), 2.31 (s, 3H), 2.12 (s, 3H) ppm.

Example 38

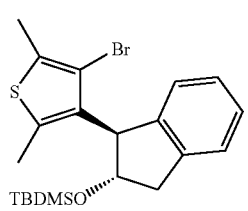

The synthesis is carried out by a method analogous to Example 6.
Yield: 94%
$^1$H NMR (CDCl$_3$): δ=7.17–7.30 (m, 3H), 6.88–7.03 (m, 1H), 5.09–5.18 (m, 1H$^a$), 4.69–4.87 (m, 2H$^b$), 4.57 (d, J=8 Hz, 1H$^a$), 3.28–3.43 (m, 1H), 3.08 (dd, J=9, 16 Hz, 1H), 2.56 (s, 3H$^a$), 2.50 (s, 3H$^b$), 2.40 (s, 3H$^a$), 2.00 (s, 3H$^b$), 0.95 (s, 9H), 0.00 (s, 3H), −0.06 (s, 3H) ppm.

Example 39

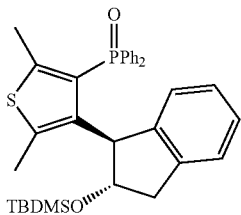

The synthesis is carried out by a method analogous to Example 21.
Yield: 74%
$^1$H NMR (d$^6$-DMSO): δ=7.69–7.87 (m, 10H), 7.36 (d, J=8 Hz, 1H), 7.30 (t, J=9 Hz, 1H), 7.23 (t, J=8 Hz, 1H), 6.77 (d, J=9 Hz, 1H), 5.60 (d, J=9 Hz, 1H), 5.00 (q, J=9 Hz, 1H), 3.40 (dd, J=9, 17 Hz, 1H), 2.84 (dd, J=9, 17 Hz, 1H), 2.08 (s, 3H), 2.02 (s, 3H), 0.98 (s, 9H), 0.06 (s, 3H), 0.00 (s, 3H) ppm.

Example 40

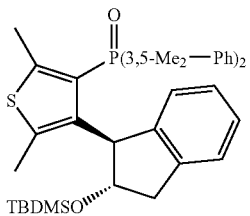

The synthesis is carried out by a method analogous to Example 21.
Yield: 65%
$^1$H NMR (d$^6$-DMSO): δ=7.28–7.44 (m, 9H), 6.86–6.90 (m, 1H), 5.20 (d, J=8 Hz, 1H), 4.96 (q, J=9 Hz, 1H), 3.39 (dd, J=8, 15 Hz, 1H), 2.75 (dd, J=10, 15 Hz, 1H), 2.50 (s, 6H), 2.46 (s, 6H), 2.12 (s, 3H), 2.08 (s, 3H), 1.00 (s, 9H), 0.05 (s, 3H), 0.00 (s, 3H) ppm.

Example 41

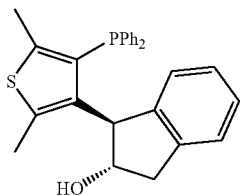

The synthesis is carried out by a method analogous to Example 23.
Yield: 77%
$^1$H NMR (d$^6$-DMSO): δ=6.80–7.40 (m, 13H), 6.60 (d, J=8 Hz, 1H), 4.60–5.00 (m, 2H), 3.30 (dd, J=8, 16 Hz, 1H), 2.85 (dd, J=7, 16 Hz, 1H), 2.10 (br s, 3H), 1.80 (s, 3H) ppm.
$^{31}$P NMR (d$^6$-DMSO): δ=–23.4, –26.9 ppm.

Example 42

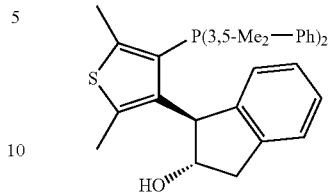

The synthesis is carried out by a method analogous to Example 23.
Yield: 77%
$^1$H NMR (d$^6$-DMSO): δ=7.13 (d, J=8 Hz, 1H), 7.05 (t, J=8 Hz, 1H), 6.71–6.95 (m, 7H), 6.55 (d, J=9 Hz, 1H), 4.58–4.90 (m, 2H), 3.32 (dd, J=9, 17 Hz, 1H), 2.81 (dd, J=8, 17 Hz, 1H), 2.25 (s, 6H), 2.21 (s, 6H), 2.10 (br s, 3H), 1.90 (s, 3H) ppm.
$^{31}$P NMR (d$^6$-DMSO): δ=–23.0, –26.7 ppm.

Example 43

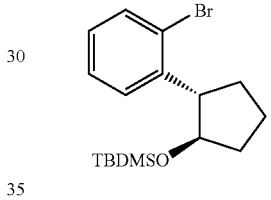

The synthesis is carried out by a method analogous to Example 7.
Yield: 96%
$^1$H NMR (CDCl$_3$): δ=7.69 (d, J=9 Hz, 1H), 7.40–7.43 (m, 1H), 7.35 (dd, J=9, 2 Hz, 1H), 7.18 (dt, J=8, 2 Hz, 1H), 4.38 (q, J=7 Hz, 1H), 3.67 (q, J=8 Hz, 1H), 2.33–2.42 (m, 1H), 1.83–2.19 (m, 5H), 0.96 (s, 9H), 0.03 (s, 3H), 0.00 (s, 3H) ppm.

Example 44

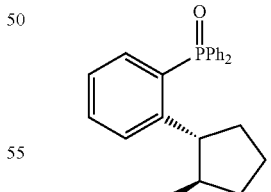

The synthesis is carried out by a method analogous to Example 21.
Yield: 56%
$^1$H NMR (C$_6$H$_6$): δ=7.77–7.83 (m, 2H), 7.66–7.72 (m, 2H), 7.13–7.20 (m, 1H), 6.93–7.08 (m, 8H), 6.72–6.78 (m, 1H), 4.35 (q, J=8 Hz, 1H), 4.22–4.31 (m, 1H), 2.22–2.33 (m, 1H), 1.20–1.82 (m, 5H), 0.92 (s, 9H), 0.00 (s, 6H) ppm.
$^{31}$P NMR (C$_6$H$_6$): δ=43.4 ppm.

Example 45

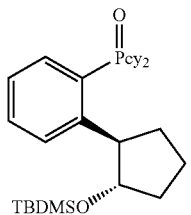

The synthesis is carried out by a method analogous to Example 21.

Yield: 56%

$^1$H NMR (C$_6$H$_6$): δ=7.09–7.20 (m, 3H), 6.91 (t, J=8 Hz, 1H), 4.70–4.81 (m, 1H), 4.30 (q, J=9 Hz, 1H), 2.50–2.61 (m, 1H), 2.16–2.25 (m, 1H), 0.95–2.00 (m, 26H), 0.87 (s, 9H), 0.00 (s, 3H), −0.09 (s, 3H) ppm.

$^{31}$P NMR (C$_6$H$_6$): δ=62.8 ppm.

Example 46

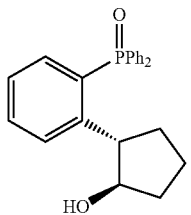

The synthesis is carried out by a method analogous to Example 12.

Yield: 67%

$^1$H NMR (C$_6$H$_6$): δ=7.62 (m, 4H), 7.21–7.29 (m, 1H), 6.96–7.12 (m, 8H), 6.79 (t, J=8 Hz, 1H), 6.46 (br s, 1H), 4.32 (q, J=8 Hz, 1H), 4.05 (q, J=10 Hz, 1H), 1.95–2.12 (m, 2H), 1.55–1.77 (m, 4H) ppm.

$^{31}$P NMR (C$_6$H$_6$): δ=48.2 ppm.

Example 47

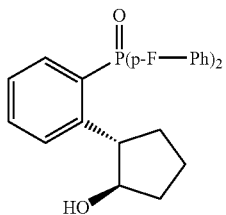

The synthesis is carried out by a method analogous to Example 21.

Yield: 45%

$^1$H NMR (C$_6$H$_6$): δ=7.38–7.49 (m, 4H), 7.25–7.31 (m, 2H), 6.86–6.92 (m, 2H), 6.63–6.75 (m, 4H), 6.30 (br s, 1H), 4.33 (q, J=8 Hz, 1H), 3.90–4.00 (m, 1H), 1.99–2.17 (m, 2H), 1.60–1.80 (m, 4H) ppm.

$^{31}$P NMR (C$_6$H$_6$): δ=42.0 ppm.

Example 48

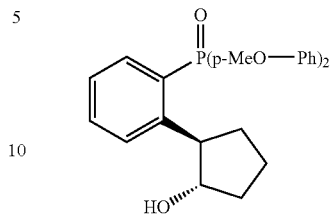

The synthesis is carried out by a method analogous to Example 21.

Yield: 57%

$^1$H NMR (C$_6$H$_6$): δ=7.52–7.62 (m, 4H), 7.21–7.28 (m, 1H), 7.02–7.18 (m, 2H), 6.81 (t, J=8 Hz, 1H), 6.53–6.60 (m, 4H), 4.30 (q, J=8 Hz, 1H), 4.10 (q, J=9 Hz, 1H), 3.11 (s, 3H), 3.06 (s, 3H), 1.92–2.06 (m, 2H), 1.60–1.80 (m, 2H), 1.25–1.36 (m, 2H) ppm.

$^{31}$P NMR (C$_6$H$_6$): δ=47.9 ppm.

Example 49

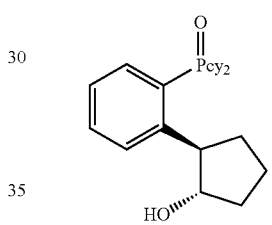

The synthesis is carried out by a method analogous to Example 12.

Yield: 67%

$^1$H NMR (C$_6$H$_6$): δ=7.42 (dd, J=10, 4 Hz, 1H), 7.25–7.32 (m, 1H), 7.01–7.09 (m, 2H), 6.45 (br s, 1H), 4.76 (q, J=9 Hz, 1H), 4.25 (q, J=7 Hz, 1H), 2.42–2.50 (m, 1H), 0.90–2.30 (m, 27H) ppm.

$^{31}$P NMR (C$_6$H$_6$): δ=66.5 ppm.

Example 50

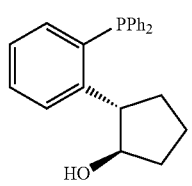

The synthesis is carried out by a method analogous to Example 23.

Yield: 57%

$^1$H NMR (C$_6$H$_6$): δ=7.54–7.62 (m, 4H), 7.30–7.39 (m, 3H), 7.24–7.29 (m, 6H), 7.15 (dt, J=9, 2 Hz, 1H), 4.26–4.40 (m, 2H), 2.23–2.32 (m, 1H), 2.02–2.11 (m, 1H), 1.67–1.91 (m, 4H), 1.60 (br s, 1H) ppm.

$^{31}$P NMR (C$_6$H$_6$): δ=0.0 ppm.

Example 51

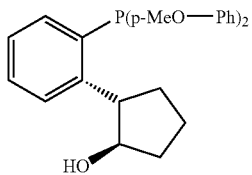

The synthesis is carried out by a method analogous to Example 23.

Yield: 37%

$^1$H NMR (C$_6$H$_6$): δ=7.40–7.48 (m, 4H), 7.21–7.31 (m, 3H), 7.12 (dt, J=9, 2 Hz, 1H), 6.81 (d, J=11 Hz, 4H), 4.16–4.31 (m, 2H), 3.31 (s, 3H), 3.30 (s, 3H), 2.15–2.25 (m, 1H), 1.92–2.03 (m, 1H), 1.59–1.85 (m, 4H), 1.56 (br s, 1H) ppm.

$^{31}$P NMR (C$_6$H$_6$): δ=−5.3 ppm.

Example 52

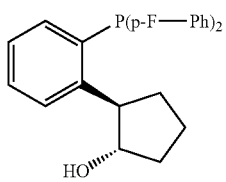

The synthesis is carried out by a method analogous to Example 23.

Yield: 60%

$^1$H NMR (C$_6$H$_6$): δ=7.00–7.05 (m, 1H), 6.92–7.03 (m, 5H), 6.80–6.90 (m, 2H), 6.55–6.63 (m, 4H), 4.00 (q, J=7 Hz, 1H), 3.85 (quin, J=8 Hz, 1H), 1.82–1.91 (m, 1H), 1.69–1.78 (m, 1H), 1.27–1.60 (m, 4H) ppm.

$^{31}$P NMR (C$_6$H$_6$): δ=−3.0 ppm.

Example 53

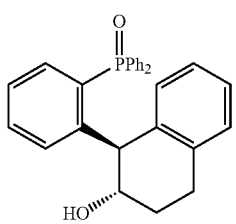

The synthesis is carried out by a method analogous to Example 21 and Example 12.

Yield: 45%

$^1$H NMR (C$_6$H$_6$): δ=7.80–7.94 (m, 4H), 6.91–7.21 (m, 13H), 6.70 (d, J=9 Hz, 1H), 6.51 (d, J=9 Hz, 1H), 5.49 (d, J=10 Hz, 1H), 4.32–4.40 (m, 1H), 2.90–3.00 (m, 1H), 2.84 (dt, J=16, 6 Hz, 1H), 2.50–2.58 (m, 1H), 2.12–2.23 (m, 1H) ppm.

$^{31}$P NMR (C$_6$H$_6$): δ=48.2 ppm.

Example 54

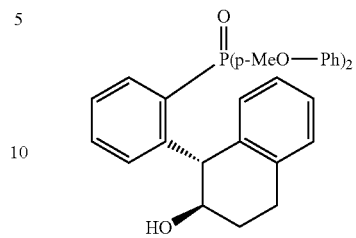

The synthesis is carried out by a method analogous to Example 21 and Example 12.

Yield: 52%

$^1$H NMR (C$_6$H$_6$): δ=7.86–7.99 (m, 4H), 7.38–7.43 (m, 1H), 7.30–7.36 (m, 2H), 7.00–7.20 (m, 5H), 6.90 (dd, J=12, 3 Hz, 2H), 6.83 (dd, J=12, 3 Hz, 2H), 6.70 (d, 9 Hz, 1H), 5.69 (d, J=10 Hz, 1H), 4.42–4.51 (m, 1H), 3.43 (s, 3H), 3.30 (s, 3H), 3.00–3.12 (m, 1H), 2.94 (dt, J=16, 4 Hz, 1H), 2.60–2.69 (m, 1H), 2.30 (ddd, J=18, 12, 6 Hz, 1H) ppm.

$^{31}$P NMR (C$_6$H$_6$): δ=48.1 ppm.

Example 55

The synthesis is carried out by a method analogous to Example 21 and Example 12.

Yield: 43%

$^1$H NMR (C$_6$H$_6$): δ=7.42–7.50 (m, 2H), 7.32–7.41 (m, 2H), 6.99–7.05 (m, 2H), 6.78–6.94 (m, 4H), 6.63 (dt, J=9, 3 Hz, 2H), 6.54 (dt, J=9, 3 Hz, 2H), 6.29 (d, J=8 Hz, 1H), 6.25 (d, J=8 Hz, 1H), 5.20 (d, J=8 Hz, 1H), 4.10–4.20 (m, 1H), 2.64–2.83 (m, 2H), 2.31–2.39 (m, 1H), 2.01 (ddd, J=18, 12, 6 Hz, 1H) ppm.

$^{31}$P NMR (C$_6$H$_6$): δ=46.8 ppm.

Example 56

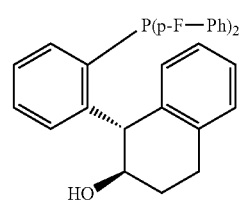

The synthesis is carried out by a method analogous to Example 23.

Yield: 50%

¹H NMR (C₆H₆): δ=7.05–7.15 (m, 5H), 6.85–7.01 (m, 6H), 6.65–6.76 (m, 5H), 5.06–5.20 (m, 1H), 4.09–4.18 (m, 1H), 2.68–2.85 (m, 2H), 1.91–2.00 (m, 1H), 1.63–1.74 (m, 1H), 1.37 (d, J=5 Hz, 1H) ppm.
$^{31}$P NMR (C₆H₆): δ=−4.1 ppm.

Example 57

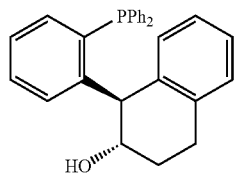

The synthesis is carried out by a method analogous to Example 23.
Yield: 45%
¹H NMR (C₆H₆): δ=7.48–7.55 (m, 5H), 7.32–7.38 (m, 1H), 7.12–7.20 (m, 6H), 6.99–7.11 (m, 5H), 6.91 (d, J=7 Hz, 1H), 5.31–5.41 (m, 1H), 4.28–4.37 (m, 1H), 2.78–2.98 (m, 2H), 2.03–2.12 (m, 1H), 1.73–1.86 (m, 1H), 1.73 (s, 1H) ppm.
$^{31}$P NMR (C₆H₆): δ=0.0 ppm.

Example 58

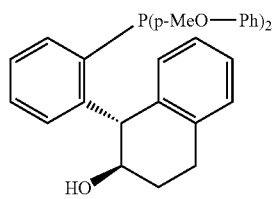

The synthesis is carried out by a method analogous to Example 23.
Yield: 53%
¹H NMR (C₆H₆): δ=7.32–7.40 (m, 4H), 7.25–7.30 (m, 1H), 6.94–6.99 (m, 4H), 6.86–6.92 (m, 2H), 6.82 (d, J=7 Hz, 1H), 6.70 (d, J=8 Hz, 4H), 5.26–5.33 (m, 1H), 4.19–4.25 (m, 1H), 3.19 (s, 6H), 2.81 (dt, J=16, 6 Hz, 1H), 2.63–2.74 (m, 1H), 1.96–2.04 (m, 1H), 1.63–1.77 (m, 2H) ppm.
$^{31}$P NMR (C₆H₆): δ=−4.4 ppm.

Example 59

(3R,4S)-4-(4-{1,1-Di[3,5-di(trifluoromethyl)phenyl]phosphino}-2,5-dimethyl-3-thienyl)tetrahydro-3-furanyl diphenylphosphinite Ethylmagnesium bromide (1 M in THF; 0.102 mmol) is added to a solution of 1-(t-butyl-1,1-dimethylsilyl) (3R,4S)-4-(4-(1,1-di(3,5-di(trifluoromethyl)phenyl)phosphino)-2,5-dimethyl-3-thienyl)tetrahydro-3-furanyl ether (0.107 mmol) in toluene while cooling in ice and the mixture is stirred for 1 hour. Chlorodiphenylphosphine (0.107 mmol) is subsequently added dropwise to this solution and the mixture is warmed to RT overnight. After filtration through aluminum oxide and removal of the solvent, the product is isolated in a yield of 77%.

¹H NMR (C₆H₆): δ=8.11 (d, 2H), 8.06 (d, 2H), 7.9 (s, 2H), 7.77–7.68 (m, 4H), 7.38–7.24 (m, 6H), 5.50–5.40 (m, 1H), 4.49–4.31 (m, 4H), 4.13 (t, 1H), 2.03 (s, 3H), 1.75 (s, 3H) ppm.
$^{31}$P NMR (C₆H₆) δ=127.9 (s, 1P), −9.9 (s, 1P) ppm.

Examples 60–89

Are Carried Out by a Method Analogous to Example 59

| Ex. | R1 | R2 | Yield [%] | $^{31}$P—NMR [ppm] |
|---|---|---|---|---|
| 60 | Ph | C₆H₁₁ | 47 | 126.6; 0.0 |
| 61 | 2-Me—Ph | C₆H₁₁ | 78 | 115.1; 0.0 |
| 62 | 3,5-Me—Ph | C₆H₁₁ | 92 | 128.0; −1.0 |
| 63 | i-Pr | C₆H₁₁ | 61 | 165.1; 0.0 |
| 64 | 4-F—Ph | C₆H₁₁ | 68 | 125.9; −1.6 |
| 65 | C₆H₁₁ | Ph | 57 | 151.4; −9.5 |
| 66 | i-Pr | Ph | 67 | 162.3; −9.4 |
| 67 | 4-F—Ph | Ph | 35 | 121.1; −9.2 |
| 68 | Ph | Ph | 80 | 123.2; −9.0 |
| 69 | 3,5-Me—Ph | Ph | 53 | 125.0; −8.6 |
| 70 | C₆H₁₁ | Ph | 62 | 160.7; −8.6 |
| 71 | Ph | Ph | 68 | 126.7; −8.4 |
| 72 | i-Pr | 3,5-Me—Ph | 52 | 164.5; −8.4 |
| 73 | Ph | 3,5-Me—Ph | 57 | 127.4; −8.0 |
| 74 | 4-F—Ph | 3,5-Me—Ph | 51 | 120.3; −9.0 |
| 75 | C₆H₁₁ | Ph | 65 | 159.9; 0.0 |
| 76 | i-Pr | Ph | 71 | 164.7; 0.0 |
| 77 | 4-F—Ph | Ph | 79 | 123.4; 0.3 |
| 78 | 2-Me—Ph | Ph | 80 | 113.7; 0.0 |
| 79 | 3,5-MePh | 4-MeO—Ph | 87 | 125.9; −2.9 |

-continued

| Ex. | R1 | R2 | Yield [%] | $^{31}$P—NMR [ppm] |
|---|---|---|---|---|

Structure: phenyl with P(R2)₂ ortho to cyclopentyl bearing (R1)₂PO

| 80 | Ph | C₆H₁₁ | 48 | 125.3; 0.0 |
| 81 | 4-F—Ph | C₆H₁₁ | 69 | 123.8; −1.0 |
| 82 | C₆H₁₁ | C₆H₁₁ | 68 | 158.3; 0.0 |
| 83 | 2-Me—Ph | Ph | 80 | 113.7; 0.0 |
| 84 | 4-F—Ph | 4-F—Ph | 79 | 122.6; −3.5 |

Structure: phenyl with P(R2)₂ ortho to tetrahydronaphthyl bearing (R1)₂PO

| 85 | Ph | Ph | 75 | 124.4; −0.0 |
| 86 | 4-F—Ph | Ph | 77 | 122.6; −1.5 |
| 87 | i-Pr | Ph | 74 | 157.4; 0.0 |
| 88 | 4-F—Ph | 4-F—Ph | 70 | 121.9; −4.2 |
| 89 | i-Pr | 4-F—Ph | 68 | 155.5; −4.4 |

Example 90

Hydrogenations

General Method of Hydrogenating Methyl Acetamido-cinnamate 0.6 μmol of Rh(COD)₂OTf and 0.66 μmol of ligand are stirred in 1 ml of methanol for 10 minutes. 300 μmol of methyl acetamidocinnamate (in 1 ml of methanol) are added to this solution. The reaction mixture is stirred at room temperature under 5 bar of hydrogen for 2 hours in an autoclave. The reaction mixture is filtered through silica gel and the enantiomeric excess is determined on the crude product by means of HPLC.

General Method of Hydrogenating Methyl Itaconate 0.6 μmol of Rh(COD)₂OTf and 0.66 μmol of ligand are stirred in 1 ml of methanol for 10 minutes. 300 μmol of methyl itaconate (in 1 ml of methanol) are added to this solution. The reaction mixture is stirred at 40° C. under 50 bar of hydrogen for 3 hours in an autoclave. The reaction mixture is filtered through silica gel and the enantiomeric excess is determined on the crude product by means of HPLC.

General Method of Hydrogenating N-acetyl-2-phenyl-1-ethenylamine 0.6 μmol of Rh(COD)₂OTf and 0.66 μmol of ligand are stirred in 1 ml of methanol for 10 minutes. 300 μmol of N-acetyl-2-phenyl-1-ethenylamine (in 1 ml of methanol) are added to this solution. The reaction mixture is stirred at 40° C. under 10 bar of hydrogen for 2 hours in an autoclave. The reaction mixture is filtered through silica gel and the enantiomeric excess is determined on the crude product by means of HPLC.

Ligand type A (dimethylthiophene with P(R2)₂ and tetrahydrofuranyl bearing (R1)₂PO)

| Ligand type A | | % ee | | |
|---|---|---|---|---|
| R1 | R2 | Methyl acetamido-cinnamate | Methyl itaconate | N-acetyl-2-phenyl-1-ethenylamine |
| 2-Me—Ph | Ph | 28 | 26 | 46 |
| 2-Me—Ph | 4-F—Ph | 31 | 29 | 15 |
| 3,5-Me—Ph | 4-F—Ph | 3 | 13 | 36 |
| C₆H₁₁ | 4-F—Ph | 24 | −3 | 34 |
| i-Pr | 4-F—Ph | 29 | −11 | 35 |
| 2-Me—Ph | 3,5-Me—Ph | 47 | 13 | 63 |
| 3,5-Me—Ph | 3,5-Me—Ph | 2 | 34 | 57 |
| C₆H₁₁ | 3,5-Me—Ph | 25 | −6 | 34 |
| i-Pr | 3,5-Me—Ph | 6 | −15 | 37 |
| i-Pr | 3,5-CF₃—Ph | −39 | 2 | 41 |
| Ph | 2-Me—Ph | −28 | −6 | −12 |
| 3,5-Me—Ph | C₆H₁₁ | −57 | — | 27 |

Ligand type B (dimethylthiophene with P(R2)₂ and cyclohexyl bearing (R1)₂PO)

| Ligand type B | | % ee | | |
|---|---|---|---|---|
| R1 | R2 | Methyl acetamido-cinnamate | Methyl itaconate | N-acetyl-2-phenyl-1-ethenylamine |
| C₆H₁₁ | Ph | 22 | 2 | −1 |
| Ph | Ph | 68 | 8 | 12 |
| 4-F—Ph | Ph | 69 | 21 | 10 |
| 3,5-Me—Ph | Ph | 69 | −3 | 7 |

Ligand type C (dimethylthiophene with P(R2)₂ and indanyl bearing (R1)₂PO)

| Ligand type C | | % ee | | |
|---|---|---|---|---|
| R1 | R2 | Methyl acetamido-cinnamate | Methyl itaconate | N-acetyl-2-phenyl-1-ethenylamine |
| Ph | 3,5-Me—Ph | −14 | 0 | 45 |
| C₆H₁₁ | Ph | 7 | 11 | 34 |

-continued

| | | | | |
|---|---|---|---|---|
| Ph | Ph | 8 | 2 | 61 |

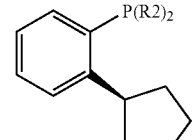

Ligand type D

| Ligand type D | | % ee | | |
|---|---|---|---|---|
| | | Methyl acetamido- | Methyl | N-acetyl-2-phenyl-1- |
| R1 | R2 | cinnamate | itaconate | ethenylamine |
| 4-F—Ph | 4-F—Ph | 15 | 3 | 65 |

The invention claimed is:

1. A bidentate organophosphorus ligand of the formula (Ia) or (Ib),

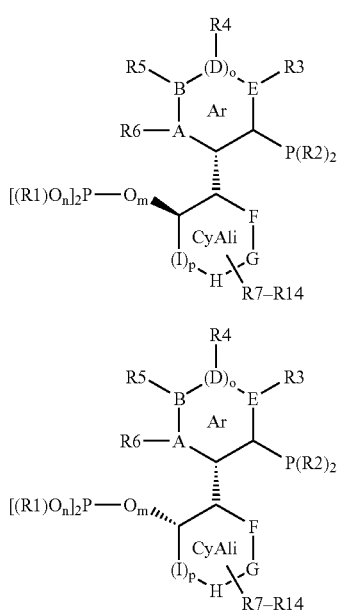

wherein
- o and p can each be, independently of one another, 0 or 1,
- Ar is part of a six-membered aromatic ring system or a 5–6-membered heteroaromatic ring system, wherein the heteroaromatic ring system can contain 1–3 nitrogen atoms, 1 oxygen atom or 1 sulfur atom in the positions A, B, D and E,
- CyAli is part of a 5–6-membered cycloaliphatic or heterocycloaliphatic ring system, wherein the hetercycloaliphatic ring system can contain 1–2 heteroatoms from the group consisting of N, O and S in the positions F, G, H and I,
- $R^1$–$R^2$ are each, independently of one another, $C_1$–$C_{24}$-alkyl, $C_3$–$C_8$-cycloalkyl, wherein the ring may also contain 1–2 heteroatoms selected from the group consisting of N, O and S; $C_6$–$C_{14}$-aryl, phenyl, naphthyl, fluorenyl, $C_2$–$C_{13}$-heteroaryl in which the number of heteroatoms selected from the group consisting of N, O, and S can be 1–4, wherein the abovementioned groups may each be, independently of one another, monosubstituted or polysubstituted by hydrogen, $C_1$–$C_{20}$-alkyl, $C_2$–$C_{20}$-alkenyl, $C_1$–$C_{10}$-haloalkyl, $C_3$–$C_8$-cycloalkyl, $C_2$–$C_9$-heteroalkyl, $C_6$–$C_8$-aryl, phenyl, naphthyl, fluorenyl, $C_2$–$C_6$-heteroaryl, wherein the number of heteroatoms from the group consisting of N, O, and S can be 1–4, $C_1$–$C_{10}$-alkoxy, $C_1$–$C_9$-trihalomethylalkyl, halo, hydroxy, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-alkyl$_2$-$C_1$–$C_8$, N-aryl$_2$-$C_5$–$C_6$, N-alkyl$_3$-$C_1$–$C_8^+$, N-aryl$_3$-$C_5$–$C_6^+$, NH—CO-alkyl-$C_1$–$C_8$, NH—CO-aryl-$C_5$–$C_6$, cyano, carboxylato of the formulae COOH and COOQ, wherein Q is either a monovalent cation or $C_1$–$C_8$-alkyl; $C_1$–$C_6$-acyloxy, sulfinato, sulfonato of the formulae $SO_3H$ and $SO_3Q$, wherein Q is either a monovalent cation, $C_1$–$C_8$-alkyl or $C_6$-aryl; phosphato of the formulae $PO_3H_2$, $PO_3HQ$ and $PO_3Q_2$, wherein Q is either a monovalent cation, $C_1$–$C_8$-alkyl or $C_6$-aryl; tri-$C_1$–$C_6$-alkylsilyl, wherein $R^1$ or $R^2$ together with the adjacent phosphorus atom may be joined to form a 4–8-membered aliphatic ring which may be substituted by linear or branched $C_1$–$C_{10}$-alkyl, $C_6$-aryl, benzyl, $C_1$–$C_{10}$-alkoxy, hydroxy or benzyloxy, $R^3$–$R^{14}$ are each, independently of one another, a hydrogen atom or $C_1$–$C_{24}$-alkyl, $C_1$–$C_{10}$-haloalkyl, $C_3$–$C_8$-cycloalkyl, $C_3$–$C_8$-cycloalkenyl, wherein the ring may also contain 1–2 heteroatoms from the group consisting of N, O and S; $C_6$–$C_{14}$-aryl, phenyl, naphthyl, fluorenyl, $C_2$–$C_{13}$-heteroaryl, wherein the number of heteroatoms selected from the group consisting of N, O, and S can be 1–4, wherein the abovementioned groups may each be, independently of one another, monosubstituted or polysubstituted by hydrogen, $C_1$–$C_{20}$-alkyl, $C_2$–$C_{20}$-alkenyl, $C_1$–$C_{10}$-haloalkyl, $C_3$–$C_8$-cycloalkyl, $C_3$–$C_8$-cycloalkenyl, $C_2$–$C_9$-heteroalkyl, $C_1$–$C_9$-heteroalkenyl, $C_6$–$C_8$-aryl, phenyl, naphthyl, fluorenyl, $C_2$–$C_6$-heteroaryl, wherein the number of heteroatoms, in particular selected from the group consisting of N, O, and S, can be 1–4, $C_1$–$C_{10}$-alkoxy, $C_1$–$C_9$-trihalomethylalkyl, trifluoromethyl, trichloromethyl, fluoro, chloro, bromo, iodo, hydroxy, trifluoromethylsulfonato, oxo, thio, thiolato, amino, $C_1$–$C_8$-substituted amino of the formulae $NH_2$, NH-alkyl-$C_1$–$C_8$, NH-aryl-$C_5$–$C_6$, N-alkyl$_2$-$C_1$–$C_8$, N-aryl$_2$-$C_5$–$C_6$, N-alkyl$_3$-$C_1$–$C_8^+$, N-aryl$_3$-$C_5$–$C_6^+$, NH—CO-alkyl-$C_1$–$C_8$, NH—CO-aryl-$C_5$–$C_6$, cyano, carboxylato of the formulae COOH and COOQ, wherein Q is either a monovalent cation or $C_1$–$C_8$-alkyl; $C_1$–$C_6$-acyloxy, sulfinato, sulfonato of the formulae $SO_3H$ and $SO_3Q$, wherein Q is either a monovalent cation, $C_1$–$C_8$-alkyl or $C_6$-aryl; phosphato of the formulae $PO_3H_2$, $PO_3HQ$ and $PO_3Q_2$, wherein Q is either a monovalent cation, $C_1$–$C_8$-alkyl or $C_6$-aryl; or tri-$C_1$–$C_6$-alkylsilyl, and two of these substituents may also be bridged,
m and n are each, independently of one another, 1 or 0, and
P is a trivalent phosphorus atom.

2. The bidentate organophosphorus ligand as claimed in claim 1, wherein
the six-membered heteroaromatic ring system is a pyridyl radical, or the five-membered heteroaromatic ring system is a furyl, thiophenyl or pyrrolyl group, and/or the cycloaliphatic ring system is a cyclohexyl or cyclopentyl radical or is part of an indenyl or tetrahydronaphthyl group as part of a fused system, or the heteroaliphatic ring system is a tetrahydrofuranyl, tetrahydrothienyl, pyrrolidinyl or piperidinyl radical.

3. The bidentate organophosphorus ligand as claimed in claim 1, wherein the substituents $R^1$ and $R^2$ are each, independently of one another, 1-methylethyl, cyclohexyl, cyclopentyl, phenyl, 2-methylphenyl, 3,5-dimethylphenyl, 4-methylphenyl, 4-methoxyphenyl, 3,5-bis(trifluoromethyl)phenyl, 4-trifluoromethylphenyl, 3,5-dimethyl-4-methoxyphenyl, 4-phenoxyl, 4-dialkylamino, 2-alkylphenyl, 3-alkylphenyl, 4-alkylphenyl, 2,6-dialkylphenyl, 3,5-dialkylphenyl, 3,4,5-trialkylphenyl, 2-alkoxyphenyl, 3-alkoxyphenyl, 4-alkoxyphenyl, 2,6-dialkoxyphenyl, 3,5-dialkoxyphenyl, 3,4,5-trialkoxyphenyl, 3,5-dialkyl-4-alkoxyphenyl, 3,5-dialkyl-4-dialkylaminophenyl, 4-dialkylamino, 3,5-trifluoromethyl, 4-trifluoromethyl, 2-sulfonyl, 3-sulfonyl, 4-sulfonyl, a monohalogenated to tetrahalogenated phenyl or a monohalogenated to tetrahalogenated naphthyl.

4. The bidentate organophosphorus ligand as claimed in claim 1, which is enantiomerically enriched.

5. The bidentate organophosphorus ligand as claimed in claim 4, wherein the enantiomeric enrichment exceeds 90%.

6. The bidentate organophosphorus ligand as claimed in claim 1 having a structure

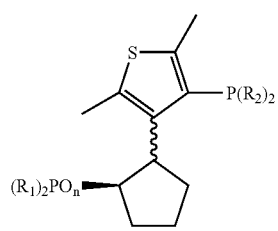

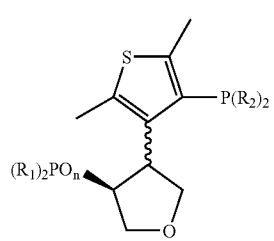

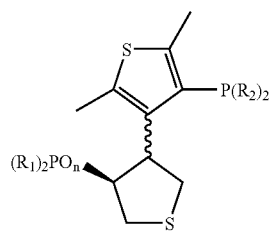

-continued

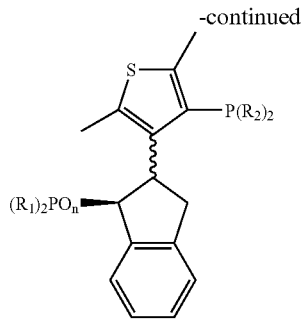

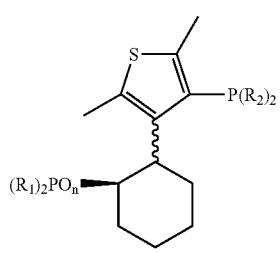

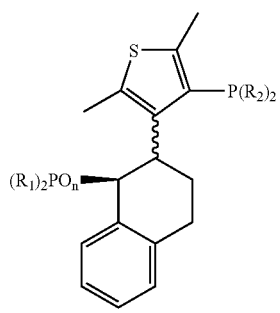

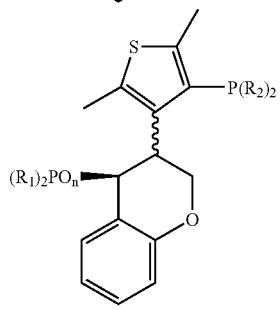

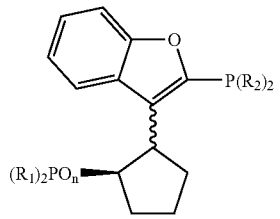

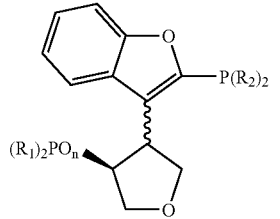

-continued
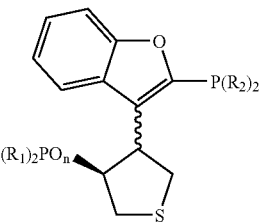
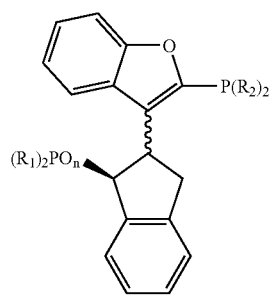
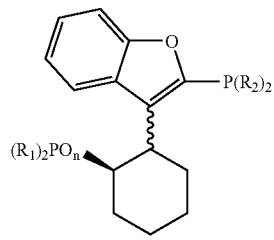
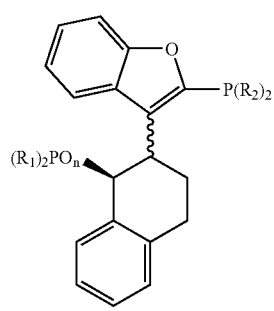
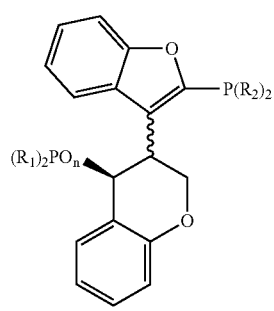
wherein n=0, or 1;
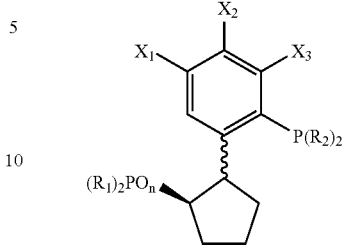
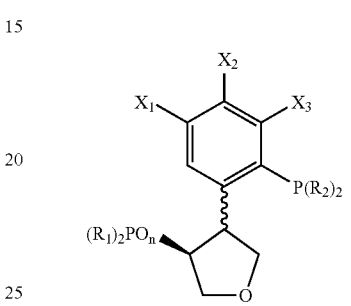
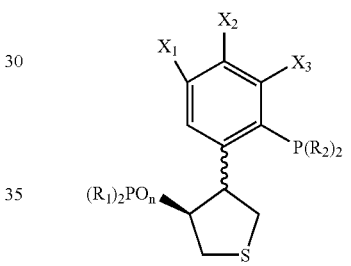
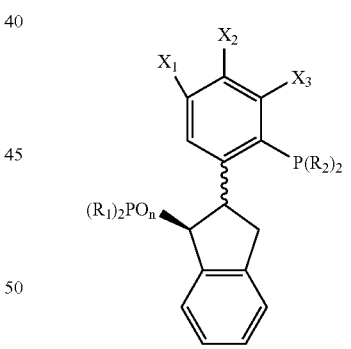
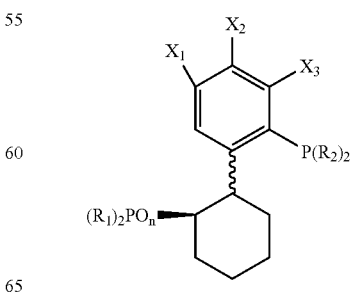

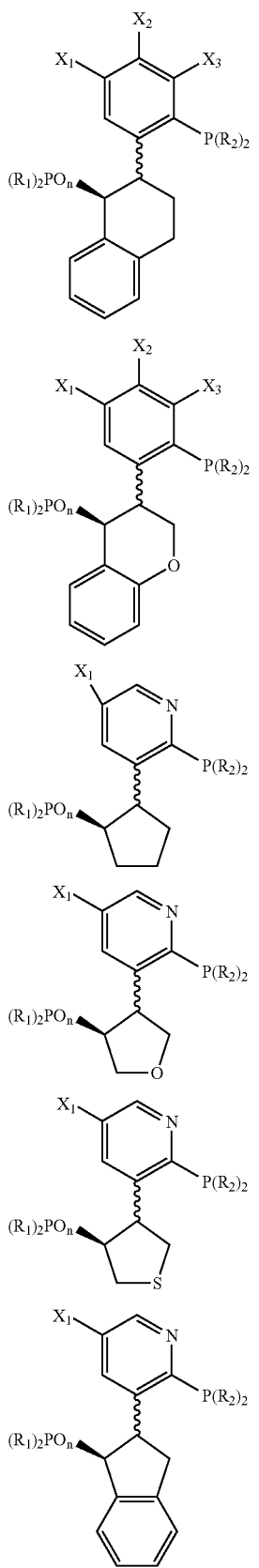
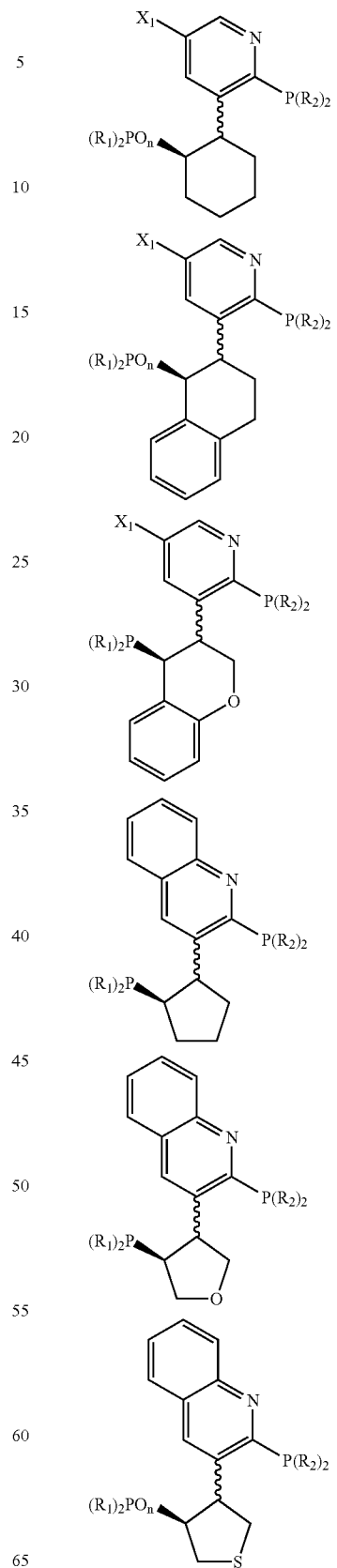

-continued
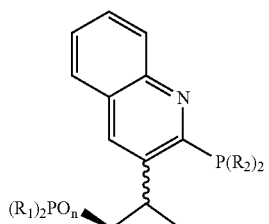
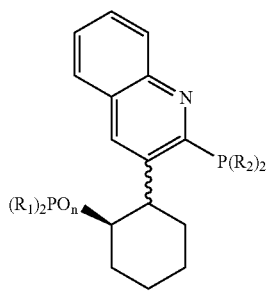
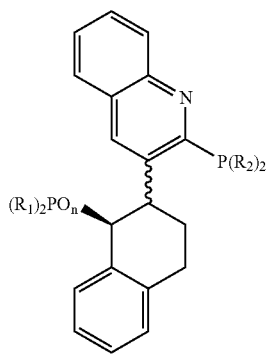
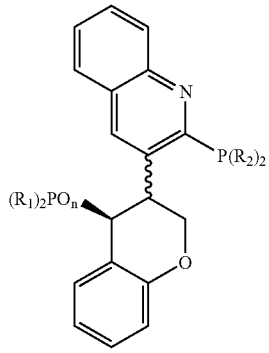
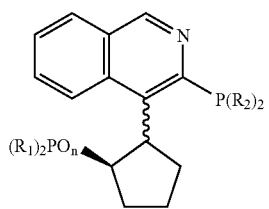
-continued
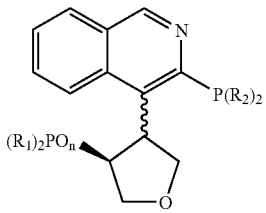
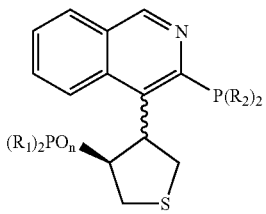
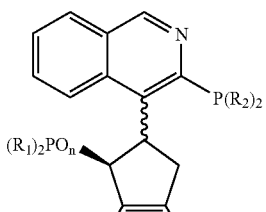
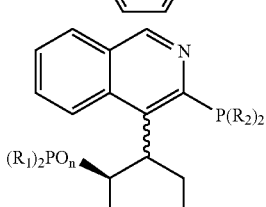
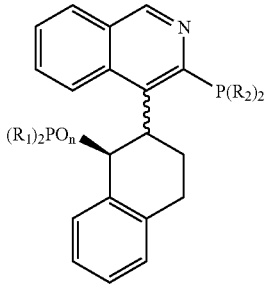
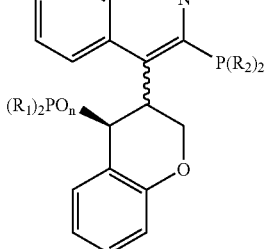
wherein $X^1$, $X^2$, $X^3$ = H, OMe, F, Me, or Et; and wherein n = 0, or 1;

-continued

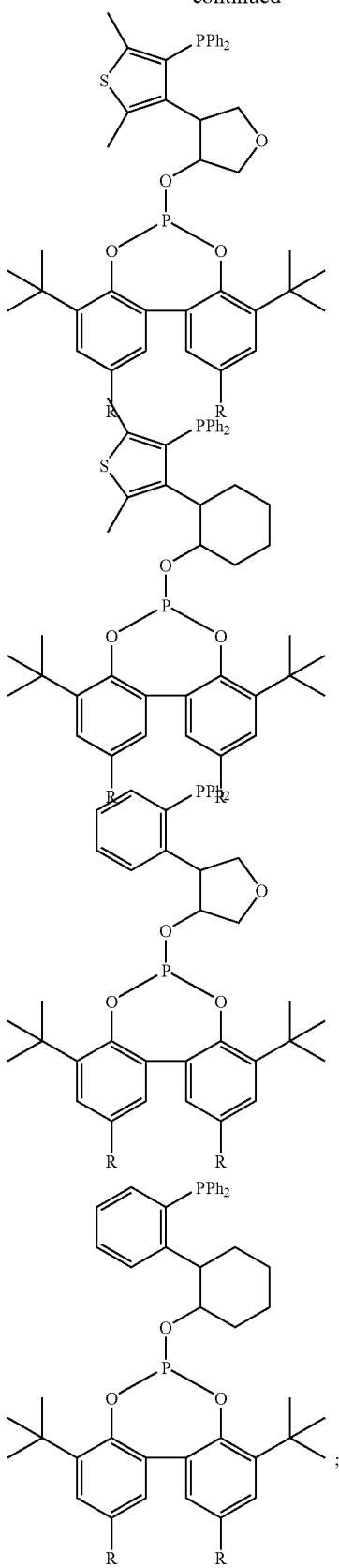

wherein R=OMe, or t-butyl.

7. A complex of the formula (II)

$$[M_xP_yL_zS_q]A_r \qquad (II)$$

wherein, in the formula (II),
M is a metal center,
L are identical or different coordinating organic or inorganic ligands,
S are coordinating solvent molecules, and
A are equivalents of noncoordinating anions, wherein
x and y are integers greater than or equal to 1,
z, q and r are integers greater than or equal to 0, the upper limit for the sum y+z+q is imposed by the number of coordination sites available on the metal centers, with not all coordination sites having to be occupied, wherein P is a bidentate organophosphorus ligand of the formula (Ia) and/or (Ib) as claimed in claim 1.

8. A complex as claimed in claim 7, characterized in that which comprises a member selected from the group consisting of palladium, platinum, rhodium, ruthenium, osmium, iridium, cobalt, nickel, copper and mixtures thereof.

9. A method for an asymmetric metal-catalyzed reaction, comprising:
contacting a complex as claimed in claim 7 as catalyst with a reactant.

10. A process for preparing a bidentate organophosphorus ligand, comprising:
a) synthesizing a basic aliphatic aromatic framework by Negishi cross-coupling of cyclic vinyl iodides with halo aromatics or by nucleophilic ring opening of a meso-epoxide with subsequent resolution of the racemate,
b) introducing a chiral phosphine unit into the basic framework by asymmetric hydroboration in a hydroboration mixture using a chiral borane, phosphination with retention or inversion of the chiral center, and
c) introducing a second phosphine group by bromine/lithium exchange using a strong lithium base and subsequent addition of a chlorophosphine;
wherein said bidentate organophosphorus ligand is defined in claim 1.

11. The process as claimed in claim 10, wherein said phosphination with retention of the chiral center is achieved by transmetallating the hydroboration mixture by diorganozinc compounds prior to the phosphination;
wherein biphosphines are obtained in said process.

12. The process as claimed in claim 10, wherein phosphination with inversion of the chiral center is achieved by working up the hydroboration mixture oxidatively to form the chiral alcohol and subsequently protecting the chiral hydroxy group, with the hydroxy group being converted after phosphination step c) into the phosphino alcohol by removal of the protective group and subsequently being phosphinated under $S_N2$ conditions;
wherein biphosphines are obtained in said process.

13. The process as claimed in claim 10, wherein phosphination with retention of the chiral center is achieved by working up the hydroboration mixture oxidatively to form the chiral alcohol and subsequently phosphinating this in the presence of a base;
wherein phosphine-phosphinites and/or phosphine-phosphites are obtained in said process.

14. The process as claimed in claim 13, wherein phosphination with inversion of the chiral center is achieved by working up the hydroboration mixture oxidatively to form the chiral alcohol and carrying out the inversion of the chiral center by means of a Mitsonubu reaction or in a two-stage process via oxidation with subsequent diastereoselective reduction.

15. The method as claimed in claim 7, wherein said asymmetric reaction is selected from the group consisting of hydrogenations, hydroformylations, rearrangements, allylic alkylations, cyclopropenation, hydrosilylations, hydrocyanations and aldol reactions.

16. The method of claim 10, wherein said basic framework comprises a chiral cycloaliphatic or heterocycloaliphatic ring system and an aromatic or heteroaromatic ring system which are linked via a direct carbon-carbon single bond.

17. The bidentate organophosphorus ligand as claimed in claim 4, wherein the enantiomeric enrichment exceeds 99%.

18. The complex as claimed in claim 7, having an octahedral, pseudooctahedral, tetrahedral, pseudotetrahedral or square planar coordination sphere which may also be distorted around the transition metal center.

19. The complex as claimed in claim 7, wherein x is 1, 2, 3, or 4.

20. The complex as claimed in claim 7, wherein S is an amine, an alcohol or an aromatic coordinating solvent molecule.

* * * * *